US012698262B2

(12) United States Patent
Buschmann et al.

(10) Patent No.: US 12,698,262 B2
(45) Date of Patent: Aug. 4, 2026

(54) POTASSIUM SALT OF 2-[(4S)-8-FLUORO-2-[4-(3-METHOXY PHENYL)PIPERAZIN-1-YL]-3-[2-METHOXY-5-(TRIFLUOROMETHYL)PHENYL]-4H-QUINAZOLIN-4-YL]ACETIC ACID

(71) Applicant: AIC246 AG & Co. KG, Wuppertal (DE)

(72) Inventors: Helmut Buschmann, Aachen (DE); Thomas Goldner, Velbert (DE); Jordi Carles Ceron Bertran, La Pobla de Montornes (ES)

(73) Assignee: AIC246 AG & Co. KG, Wuppertal (DE)

( * ) Notice: Subject to any disclaimer, the term of this patent is extended or adjusted under 35 U.S.C. 154(b) by 713 days.

(21) Appl. No.: 17/802,557

(22) PCT Filed: Mar. 1, 2021

(86) PCT No.: PCT/EP2021/055078
§ 371 (c)(1),
(2) Date: Aug. 26, 2022

(87) PCT Pub. No.: WO2021/170882
PCT Pub. Date: Sep. 2, 2021

(65) Prior Publication Data

US 2023/0150950 A1 May 18, 2023

(30) Foreign Application Priority Data

Feb. 27, 2020 (EP) .................................... 20159742

(51) Int. Cl.
*C07D 239/84* (2006.01)

(52) U.S. Cl.
CPC ........ *C07D 239/84* (2013.01); *C07B 2200/13* (2013.01)

(58) Field of Classification Search
CPC ..................................................... C07D 239/84
See application file for complete search history.

(56) References Cited

U.S. PATENT DOCUMENTS

| | | | |
|---|---|---|---|
| 7,196,086 | B2 | 3/2007 | Wunberg et al. |
| 8,816,075 | B2 | 8/2014 | Goossen et al. |
| 9,637,459 | B2 | 5/2017 | Grunenberg et al. |
| 2015/0133461 | A1 | 5/2015 | Paulus et al. |

FOREIGN PATENT DOCUMENTS

| | | | |
|---|---|---|---|
| CN | 109966244 | A | 7/2019 |
| WO | 2004096778 | A1 | 11/2004 |
| WO | 2013127970 | A1 | 9/2013 |
| WO | 2013127971 | A1 | 9/2013 |
| WO | 2021170874 | A1 | 9/2021 |
| WO | 2021170875 | A1 | 9/2021 |
| WO | 2021170878 | A1 | 9/2021 |
| WO | 2021170879 | A1 | 9/2021 |

OTHER PUBLICATIONS

International Search Report PCT/EP2021/055078 dated Apr. 6, 2021 (pp. 1-4) and Written Opinion (pp. 1-5).
Search report in corresponding EP20159742 dated Jun. 11, 2020 (pp. 1-7).

*Primary Examiner* — John S Kenyon
(74) *Attorney, Agent, or Firm* — Millen, White, Zelano & Branigan, P.C.; Brion P. Heaney

(57) ABSTRACT

The present invention relates to potassium salt of 2-[(4S)-8-fluoro-2-[4-(3-methoxyphenyl)-piperazin-1-yl]-3-[2-methoxy-5-(trifluoromethyl)phenyl]-4H-quinazolin-4-yl] acetic acid and solvates thereof. The invention further relates to methods of preparation of said potassium salt of 2-[(4S)-8-fluoro-2-[4-(3-methoxyphenyl)piperazin-1-yl]-3-[2-methoxy-5-(trifluoromethyl)-phenyl]-4H-quinazolin-4-yl] acetic acid or solvates thereof as well as pharmaceutical compositions comprising said salt.

29 Claims, 13 Drawing Sheets

POTASSIUM SALT OF 2-[(4S)-8-FLUORO-2-[4-(3-METHOXYPHENYL) PIPERAZIN-1-YL]-3-[2-METHOXY-5-(TRIFLUOROMETHYL)PHENYL]-4H-QUINAZOLIN-4-YL]ACETIC ACID

The present invention relates to a potassium salt of 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid and solvates thereof. The invention further relates to methods of preparation of said potassium salt of 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid or solvates thereof as well as pharmaceutical compositions comprising said salt. Said salt is particularly useful for treatment and/or prevention of diseases associated with cytomegalovirus (CMV), particularly human cytomegalovirus (HCMV).

BACKGROUND OF THE INVENTION

Cytomegalovirus (CMV) is a common opportunistic infection that causes significant morbidity and preventable mortality after solid-organ and allogeneic hematopoietic stem cell transplantation.

HCMV is a species of virus that belongs to the viral family known as Herpesviridae or herpes viruses. It is typically abbreviated as HCMV and is alternatively known as human herpesvirus-5 (HHV-5). Within Herpesviridae, HCMV belongs to the Betaherpesvirinae subfamily, which also includes cytomegaloviruses from other mammals.

Letermovir is known as a highly active drug for addressing HCMV infection and extensively described in Lischka et al., *In Vitro and In Vivo Activities of the Novel Anticytomegalovirus Compound Letermovir. Antimicrob. Agents Chemother.* 2010, 54: p. 1290-1297, and Kaul et al., *First report of successful treatment of multidrug-resistant cytomegalovirus disease with the novel anti-CMV compound Letermovir. Am. J. Transplant.* 2011, 11:1079-1084; as well as Marschall et al., *In Vitro Evaluation of the Activities of the Novel Anticytomegalovirus Compound Letermovir against Herpesviruses and Other Human Pathogenic Viruses. Antimicrob. Agents Chemother.* 2012, 56:1135-1137.

The precise chemical name of letermovir is 2-[(4S)-8-fluoro-2-[4-(3-methoxyphenyl)piperazin-1-yl]-3-[2-methoxy-5-(trifluoromethyl)phenyl]-4H-quinazolin-4-yl] acetic acid, as depicted below:

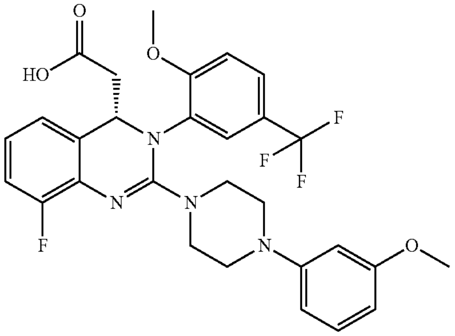 [SMILES: COc1cccc(N2CCN(C3=Nc4c(F)cccc4[C@H](CC(=O)O)N3c3cc(C(F)(F)F)ccc3OC)CC2)c1]

letermovir was developed by the applicant as an antiviral agent, in particular for combating infections caused by the human cytomegalovirus (HCMV). The synthesis of letermovir is disclosed in WO 2006/133822 and WO 2004/096778.

Salts of letermovir are described in International Publication No. WO 2013/127971. Particularly, some solvates of sodium and calcium salts of letermovir have been prepared in crystalline and amorphous form. In case of the sodium salt of letermovir, mixed alcohol water solvates, such as methanol or ethanol hydrates were obtained (example 1 of WO 2013/127971 A1), which can be converted to crystalline letermovir sodium trihydrate (example 2 of WO 2013/127971 A1).

There remains a need, however, for a stable crystalline salt of letermovir, which can be prepared in a reproducible and scalable process and which remains stable in storage over a long period of time.

DESCRIPTION OF THE INVENTION

The first aspect of the present invention relates to a crystalline potassium salt of letermovir of the following formula (I):

(I)

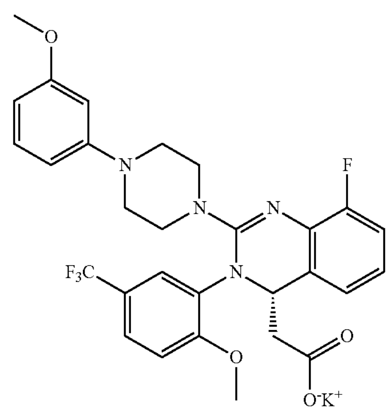

or a solvate thereof.

The crystalline potassium salt of letermovir in the context of the present invention is monopotassium salt, in which 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid and potassium counter-ion are present in equimolar ratio (1:1).

The crystalline potassium salt of letermovir can be easily prepared in high yields from a solution of letermovir in a mixture of a dialkyl ether and an alcohol with further addition of potassium hydroxide.

It has further been discovered that said crystalline potassium salt of letermovir or solvates thereof are readily soluble and also exhibit good storage stability in an aqueous medium, in particular at physiological pH. In particular, concentration levels of above 100 mg/mL in an aqueous medium can be achieved by dissolving said crystalline potassium salt of letermovir while the pH values of the final solution remain in the range 7-8, in particular 7.4-7.8.

Also, the crystalline potassium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate or solvates thereof do not contain any toxic solvent residuals, thereby rendering said compound particularly useful for the production of pharmaceutical compositions for use in methods of treatment and/or prevention of diseases associated and/or caused by cytomegalovirus (CMV), particularly human cytomegalovirus (HCMV).

Furthermore, the crystalline potassium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate or solvates thereof which are obtainable according to the invention exhibit a high degree of purity.

Another aspect of the present invention relates to a method of preparation of said potassium salt of letermovir of formula (I)

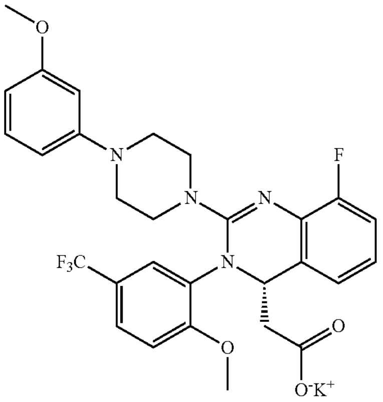

(I)

or a solvate thereof, comprising the following steps:

a) Dissolving 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid or a salt or a solvate thereof in a first solvent, wherein said first solvent comprises at least one C1-C6-dialkyl ether and/or at least one C5-C9-alkane and/or at least one C5-C9-cycloalkane and at least one C1-C6 alcohol, optionally under heating;

b) Adding potassium hydroxide to the solution obtained in step a to provide a first mixture;

c) Stirring said first mixture obtained in step b at a temperature in the range of from 25° C. to 80° C. for at least 5 minutes;

d) Cooling said first mixture to a temperature in the range of from 0° C. to 30° C. and stirring said first mixture at said temperature for at least 10 minutes;

e) Removing said first solvent to provide a first solid;

f) Contacting said first solid with a second solvent comprising at least one C1-C6-dialkyl ether and/or at least one C5-C9-alkane and/or at least one C5-C9-cycloalkane to provide a second mixture;

g) Stirring said second mixture at a temperature in the range of from 0° C. to 30° C. for at least 1 hour;

h) Removing said second solvent to provide a second solid.

The method of the present invention has following technical advantages:

The potassium salt of Letermovir can be prepared directly from Letermovir free base;

The process has a relatively short reaction time (several hours);

The process affords directly crystalline potassium salt of letermovir without any toxic solvent residuals;

The process is reproducible and suitable for further scaling-up.

The present invention further relates in one aspect to a pharmaceutical composition comprising said crystalline potassium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate or a solvate thereof.

Another aspect of the present invention relates to the use of said crystalline potassium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate or a solvate thereof or a pharmaceutical composition comprising said crystalline potassium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate or a solvate thereof for the preparation of a medicament for the treatment and/or prevention of diseases, in particular of virus infections, preferably human cytomegalovirus (HCMV) infections or infections with another member of the herpes viridae group.

Another aspect of the present invention relates to a method of treatment and/or prevention of virus infections, preferably human cytomegalovirus (HCMV) infections or infections with another member of the herpes viridae group, in a subject in need thereof by administering said crystalline potassium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate or a solvate thereof or a pharmaceutical composition comprising said crystalline potassium 2-[(4S)-8-fluoro-2-[4-(3-methoxyphenyl)-piperazin-1-yl]-3-[2-methoxy-5-(trifluoromethyl)phenyl]-4H-quinazolin-4-yl]acetate or a solvate thereof.

DETAILED DESCRIPTION

It is noted that the term "comprising" also encompasses the meaning "consisting of", e.g., a group of members comprising said members also encompasses a group of members consisting only of these members.

The term "room temperature" as used herein, is synonymous to the term "standard room temperature" and refers to a temperature in the range of from 19° C. to 26° C. For example, "stirring said mixture at room temperature" means "stirring said mixture at a temperature in the range of from 19° C. to 26° C.".

As used herein, the term "crystal" refers to any three-dimensional ordered array of molecules that diffracts X-rays.

As used herein, the term "unit cell" refers to a basic parallelepiped shaped block. The entire volume of crystal may be constructed by regular assembly of such blocks. Each unit cell comprises a complete representation of the unit of pattern, the repetition of which builds up the crystal.

As used herein, the term "space group" refers to the arrangement of symmetry elements of a crystal.

As used herein, the term "asymmetric unit" refers to a minimal set of atomic coordinates that can be used to generate the entire repetition in a crystal.

The term "polymorph" refers to a particular crystal form (i.e. structure of crystal lattice) of potassium salt of letermovir or a solvate thereof that can exist in more than one crystal form in the solid state.

As used herein, the term "solvates" refers to those forms of a compound in particular potassium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate which form a complex through coordination with solvent molecules. Hydrates are a special form of solvates in which the coordination takes place with water.

In the context of the invention, the term "stable" or "storage-stable" means, in the case of the potassium salt of letermovir or a solvate thereof according to the invention, that at 25° C. they contain a minimum proportion of >90%, preferably >95%, and most preferably 99% of 2-[(4S)-8-fluoro-2-[4-(3-methoxyphenyl)piperazin-1-yl]-3-[2-methoxy-5-(trifluoromethyl)phenyl]-4H-quinazolin-4-yl] acetic acid for a storage period of at least two, preferably at least three, even more preferably at least six weeks, and most preferred 12 months, when said salts are measured with the HPLC method as defined in the "Methods and Equipment" section.

Within the scope of the present invention the terms "obtained by" and "obtainable by" have the same meaning and are used interchangeably.

Within the scope of the present invention the term "equivalents" is understood to mean "molar equivalents".

As used herein the term "solvent" refers to a liquid or a mixture of liquids which is suitable for dissolving or solvating a component or material described herein.

As used herein the term "contacting" with respect to two materials refers to the addition of the first material to the second material or the addition of the second material to the first material. In particular, the term "contacting" refers to the addition of a solid to a solvent or the addition of a solvent to a solid.

As used herein, the term "dialkyl ether" refers to a group of formula R—O—R, wherein each of the R groups is alkyl.

As used herein, the term "alcohol" refers to a group of formula R—OH, wherein R is alkyl.

As used herein the term "alkane" refers to a saturated hydrocarbon with straight or branched chain having the number of carbon atoms designated (i.e. C5-C9-alkyl means five to nine carbon atoms). Non-limiting examples include n-pentane, isopentane, n-hexane, n-heptane, n-octane and n-nonane.

As used herein the term "alkyl" by itself or as part of another substituent refers to a radical of alkane having the number of carbon atoms designated (i.e. C1-C6-alkyl means one to six carbon atoms) and includes straight and branched chains. Non-limiting examples include methyl, ethyl, propyl, isopropyl, butyl, isobutyl, tert-butyl, pentyl, neopentyl, and hexyl. For the avoidance of doubt where two alkyl moieties are present in a group, the alkyl moieties may be the same or different.

As used herein, the term "cycloalkane" refers to cyclic aliphatic hydrocarbons containing from 1 to 3 rings and having from 3 to 12 ring carbon atoms.

As used herein the term "treatment" or "treating" is defined as the application or administration of a therapeutic agent e.g. a potassium salt of letermovir or a solvate thereof (alone or in combination with another pharmaceutical agent) to a subject, or application or administration of a therapeutic agent to an isolated tissue or cell line from a subject who has an HCMV infection, a symptom of HCMV infection, or the potential to develop an HCMV infection with the purpose to cure, heal, alleviate, relieve, alter, remedy, ameliorate, improve or affect the HCMV infection, the symptoms of HCMV infection or the potential to develop an HCMV infection. Such treatments may be specifically tailored or modified based on knowledge obtained from the field of pharmacogenomics.

As used herein the term "prevent", "preventing" or "prevention" means no disorder or disease development if none had occurred, or no further disorder or disease development if there had already been development of the disorder or disease. Also considered is the ability of one to prevent some or all of the symptoms associated with the disorder or disease. Prevention of diseases encompasses also prophylaxis of diseases.

As used herein the term "subject" refers to a human or a non-human mammal. Non-human mammals include for example livestock and pets such as ovine, bovine, porcine, feline, canine and murine mammals. Preferably the subject is human.

As used herein the term "pharmaceutically acceptable" refers to a material such as a carrier or diluent which does not abrogate the biological activity or properties of the compound and is relatively non-toxic i.e. the material may be administered to a subject without causing undesirable biological effects or interacting in a deleterious manner with any of the components of the composition in which it is contained.

The present invention relates to a crystalline potassium salt of letermovir of the following formula (I):

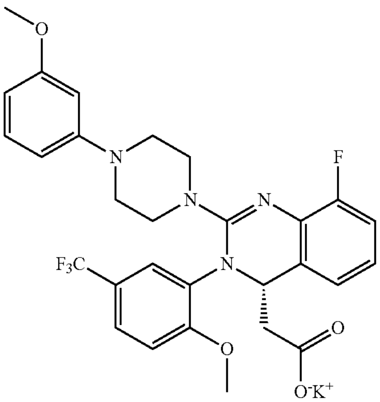

(I)

or a solvate thereof.

Surprisingly, the inventors have provided a novel potassium letermovir salt, potassium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate of formula (I), which can be obtained by dissolving the letermovir free base in a mixture of a C1-C6-dialkyl ether and/or a C5-C9-alkane and/or a C5-C9-cycloalkane and an alcohol, in particular in a mixture of diisopropyl ether and ethanol, followed by addition of potassium hydroxide. Said potassium salt can be alternatively obtained by dissolving the letermovir free base in a mixture of isopropyl acetate and diisopropyl ether followed by addition of potassium hydroxide.

Said crystalline potassium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate or a solvate thereof may be present in different polymorph forms. Polymorphs are different crystalline forms of the same compound which may have substantially different physicochemical properties, such as solubility, stability and bioavailability. Evaluation of polymorphism of a drug substance plays a crucial role in formulation study because polymorphism may impact drug behavior. For example, rate of dissolution of drug substance impacts the bioavailability of finished products. The solubility, in turn, is dependent on the polymorphic nature of the drug substance. Different polymorphs may have different solubilities and hence the corresponding drug products may have different bioavailabilities.

Different methods for examination of polymorphs can be used. Such methods include microscopy, IR-spectroscopy, Raman spectroscopy, Solid-state NMR, TGA, DSC, PXRD, PDF and other techniques. A combination of different techniques can be applied. In particular, PXRD is a powerful technique for examination of polymorphs. X-rays are reflected from crystals only when the angle between the beam and the planes in the crystal satisfies the Bragg condition. There is an infinite number of possible planes in the crystal. Each molecular repetition gives a unique set of reflections and, therefore, generates a unique pattern, which can be recorded as a spectrum.

However, conventional PXRD analysis yields the average structure of materials, e.g. average positions, displacement parameters and occupancies, and is not able to provide the information about local disorders in the material. For this purpose the Pair Distribution Function (PDF) can be used, which gives the probability of finding an atom at a certain distance from a given atom. The PDF is the Sine-Fourier transform of the total scattering diffraction pattern, which provides the information about average interatomic distances, structural disorders or distortions and average coordination properties. Therefore, the PDF is capable of distinguishing different solid forms of the same compound which are indistinguishable with conventional PXRD analysis. In particular, different amorphous forms which are characterized by different degrees of disorder can be determined by the PDF analysis (Boetker et al. Pharmaceutics 2012, 4, 93-103).

In particular, said crystalline potassium salt of letermovir or a solvate thereof is a hydrate.

Said crystalline potassium salt of letermovir was identified as a mixed water-ethanol solvate (Form A). The crystalline Form A can be obtained, in particular, by the herein described method wherein in step a 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid or a salt or a solvate thereof is dissolved in C1-C6-dialkyl ether.

The crystalline Form A of the potassium salt of letermovir was characterized by PXRD, $^1$H-NMR, DVS, TGA and DSC (see FIGS. 1-4). The X-ray diffraction pattern of said polymorph crystalline Form A of the potassium salt of letermovir comprises 2-theta angle values of 6.1, 9.4, 10.6, 11.2, 12.3, 12.8, 15.5, 16.3, 16.7, 17.8, 18.9, 19.9, 20.8, 21.7, 22.3, 23.5, 25.1, 25.9, 26.6, 27.1, 28.1, 28.5, 29.4, 30.1, 30.8, 31.2, 32.0, 32.6 and 33.3 degrees, and said 2-theta angle values have a normal deviation of ±0.1°.

In addition to the crystalline Form A of the potassium salt of letermovir, another form of potassium salt of letermovir, which is a 2.5 hydrate (Form B) was identified. The crystalline Form B was characterized by PXRD, $^1$H-NMR, DVS, TGA and DSC (see FIGS. 5-8). The X-ray diffraction pattern of said crystalline Form B of the potassium salt of letermovir comprises 2-theta angle values of 6.1, 9.5, 10.7, 11.3, 12.4, 12.9, 15.6, 16.4, 16.8, 17.9, 19.0, 20.0, 20.9, 21.7, 22.4, 23.6, 25.2, 26.0, 26.7, 27.3, 28.2, 28.7, 29.6, 30.2, 30.9, 31.4, 32.2, 32.8 and 33.4 degrees, and said 2-theta angle values have a normal deviation of ±0.1°.

The crystalline Form B can be obtained, in particular, by the herein described method, which additionally comprises the subsequent step i):

i) Keeping the second solid at a temperature in the range of from 20° C. to 30° C. and at a relative humidity of at least 60% for at least 1 hour.

Alternatively, the crystalline Form B can be obtained, in particular, by a method comprising the following steps:

a') Dissolving 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid or a salt or a solvate thereof in a first solvent, wherein said first solvent comprises at least one C1-C6-dialkyl ether and at least one C1-C6 alcohol, optionally under heating;
b') Adding potassium hydroxide to the solution obtained in step a' to provide a first mixture;
c') Stirring said first mixture obtained in step b' at a temperature in the range of from 25° C. to 80° C. for at least 5 minutes;
d') Cooling said first mixture to a temperature in the range of from 0° C. to 30° C. and stirring said first mixture at said temperature for at least 10 minutes;
e') Removing said first solvent to provide a first solid;
f') Contacting said first solid with a second solvent comprising at least one C1-C6-dialkyl ether to provide a second mixture;
g') Stirring said second mixture at a temperature in the range of from 0° C. to 30° C. for at least 1 hour;
h') Removing said second solvent to provide a second solid;
i') Dissolving said second solid in a third solvent comprising isopropyl acetate;
j') Adding at least one C1-C6-dialkyl ether to the solution obtained in step i';
k') Optionally stirring said mixture;
l') Removing said third solvent to provide a third solid.

In a preferred embodiment the method of producing the crystalline potassium salt of letermovir or a solvate thereof comprises the following steps:

a) Dissolving 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid or a salt or a solvate thereof in a first solvent, wherein said first solvent comprises at least one C1-C6-dialkyl ether and at least one C1-C6 alcohol, optionally under heating;
b) Adding potassium hydroxide to the solution obtained in step a to provide a first mixture;
c) Stirring said first mixture obtained in step b at a temperature in the range of from 25° C. to 80° C. for at least 5 minutes;
d) Cooling said first mixture to a temperature in the range of from 0° C. to 30° C. and stirring said first mixture at said temperature for at least 10 minutes;
e) Removing said first solvent to provide a first solid;
f) Contacting said first solid with a second solvent comprising at least one C1-C6-dialkyl ether to provide a second mixture;
g) Stirring said second mixture at a temperature in the range of from 0° C. to 30° C. for at least 1 hour;
h) Removing said second solvent to provide a second solid.

In one embodiment said method may further comprise a subsequent step of keeping the second solid at a temperature in the range of from 20° C. to 30° C. and at a relative humidity of at least 60% for at least 1 hour, more preferably for at least 2 hours, even more preferably for at least hours, even more preferably for at least 10 hours, even more preferably for at least 1 day, even more preferably for at least 2 days, most preferred for 3 days.

In one embodiment said C1-C6-dialkyl ether is C1-C4-dialkyl ether, preferably, diisopropyl ether. In one embodiment said C1-C6 alcohol is C1-C4-alcohol, preferably ethanol.

In one embodiment the ratio of volumes of C1-C6-dialkyl ether and C1-C6 alcohol in step a or a' is in the range of from 3:1 to 1:3. Preferably the ratio of volumes of C1-C6-dialkyl ether and C1-C6 alcohol in step a or a' is in the range of from 2:1 to 1:2. More preferably the ratio of volumes of C1-C6-dialkyl ether and C1-C6 alcohol in step a is in the range of from 1.5:1 to 1:1.5. Most preferred the ratio of volumes of C1-C6-dialkyl ether and C1-C6 alcohol in step a is about 1:1.

In one embodiment 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid or a salt or a solvate thereof is dissolved in step a or a' at a temperature in the range of from 20° C. to 60° C., preferably in the range of from 40° C. to 60° C., more preferably in the range of from 45° C. to 55° C., most preferred at about 50° C.

In one embodiment potassium hydroxide in step b or b' is added in the amount of 1 to 5 equivalents with respect to letermovir free base. In a preferred embodiment potassium hydroxide in step b or b' is added in the amount of 1 to 3 equivalents with respect to letermovir free base. In a more preferred embodiment potassium hydroxide in step b or b' is added in the amount of 1 to 2 equivalents with respect to letermovir free base. Most preferred potassium hydroxide in step b or b' is added in the amount of about 1 equivalent with respect to letermovir free base.

In one embodiment the mixture in step c or c' is stirred at a temperature in the range of from 25° C. to 80° C., preferably the range from 30° C. to 70° C., more preferably the range from 40° C. to 60° C., even more preferably the range from 45° C. to 55° C., most preferred at about 50° C. In one embodiment the mixture in step c or c' is stirred at said temperature for at least 5 minutes, more preferably for at least 10 minutes, even more preferably for at least 30 minutes, even more preferably for at least 1 hour, in particular for 2 hours. In one embodiment the mixture in step c or c' is stirred at a temperature in the range of from 45° C. to 55° C. for at least 30 minutes. In one embodiment the mixture in step c or c' is stirred at a temperature in the range of from 45° C. to 55° C. for at least 1 hour. In one embodiment the mixture in step c or c' is stirred at a temperature of about 50° C. for at least 30 minutes. In one embodiment the mixture in step c or c' is stirred at a temperature of about 50° C. for at least 1 hour.

In one embodiment the mixture in step d or d' is cooled to a temperature in the range of from 0° C. to 30° C., more preferably in the range of from 10° C. to 30° C., even more preferably in the range of from 20° C. to 30° C., most preferred to room temperature. In one embodiment the mixture in step d or d' is stirred at said temperature for at least 5 minutes, more preferably for at least 10 minutes, even more preferably for at least 30 minutes, even more preferably for at least 1 hour, in particular for 2 hours. In one embodiment the mixture in step d or d' is cooled to a temperature in the range of from 20° C. to 30° C. and stirred at said temperature for at least 30 minutes. In one embodiment the mixture in step d or d' is cooled to a temperature in the range of from 20° C. to 30° C. and stirred at said temperature for at least 1 hour.

In one embodiment said first solvent in step e or e' is removed by evaporation.

In one embodiment said second solvent in step h or h' is removed by filtration.

In one embodiment the mixture in step g or g' is stirred at a temperature in the range of from 0° C. to 30° C., more preferably the range of from 10° C. to 30° C., even more preferably in the range of from 20° C. to 30° C., most preferred to room temperature. In one embodiment the mixture in step g or g' is stirred at said temperature for at least 1 hour, more preferably for at least 2 hours, even more preferably for at least 5 hours, even more preferably for at least 10 hours, in particular for 1 day.

In a further preferred embodiment according to invention described herein, the method can further contain a step of granulating or micronizing said potassium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate or a solvate thereof.

In one aspect, the present invention further relates to a crystalline potassium salt of letermovir or a solvate thereof which is obtainable by the method disclosed herein.

Due to its properties and characteristics the potassium salt of letermovir or a solvate thereof according to the invention can be used to produce a pharmaceutical composition that is suitable for use in methods of preventing and/or treating diseases, in particular virus infections.

The following areas of indication can be mentioned, by way of example:

1) Treatment and prevention of HCMV infections in AIDS subjects (retinitis, pneumonitis, gastrointestinal infections).
2) Treatment and prevention of cytomegalovirus infections in bone marrow and organ transplant subjects who often contract life-threatening HCMV pneumonitis or encephalitis, as well as gastrointestinal and systemic HCMV infections.
3) Treatment and prevention of HCMV infections in neonates and infants.
4) Treatment of acute HCMV infection in pregnant women.
5) Treatment of HCMV infection in immune-suppressed subjects suffering from cancer and undergoing cancer therapy.
6) Treatment of HCMV-positive cancer subjects with the aim of reducing HCMV-mediated tumour progression (cf. J. Cinatl, et al., FEMS Microbiology Reviews 2004, 28, 59-77).

The inventive potassium salt of letermovir or a solvate thereof is preferably used to produce a pharmaceutical composition which is suitable for use in prevention and/or treatment of infections with a representative of the Herpes viridae group, in particular a cytomegalovirus, in particular the human cytomegalovirus.

Due to its pharmacological properties and characteristics, the crystalline potassium salt of letermovir or a solvate thereof according to the invention, can be used by themselves and, if needed, also in combination with other active substances, especially antiviral agents.

In another aspect, the present invention refers to a pharmaceutical composition comprising the crystalline potassium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate of formula (I) or a solvate thereof. Preferably, the pharmaceutical composition comprises further at least one pharmaceutically acceptable carrier, excipient and/or diluent.

As pharmaceutically acceptable carrier, excipient and/or diluents can be used carriers such as preferably an inert carrier like lactose, starch, sucrose, cellulose, magnesium stearate, dicalcium phosphate, calcium sulfate, talc, mannitol, ethyl alcohol (liquid filled capsules); suitable binders include starch, gelatin, natural sugars, corn sweeteners, natural and synthetic gums such as acacia, sodium alginate, carboxymethylcellulose, polyethylene glycol and waxes, sugars such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate; lubricants such as boric acid, sodium benzoate, sodium acetate, sodium chloride, magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine; disintegrating agents (disintegrates) such as starch, methylcellulose, guar gum, modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium crosscarmellose, alginates such as alginic acid and sodium alginate, clays such as bentonites, and effervescent mixtures; coloring agents, sweetening agents, flavoring agents, preservatives; glidents are for example silicon dioxide and talc; suitable adsorbent are clay, aluminum oxide, suitable diluents are water or water/propylene glycol solutions for parenteral injections, juice, sugars such as lactose, sucrose, mannitol, and sorbitol, starches derived from wheat, corn rice, and potato, and celluloses such as microcrystalline cellulose.

The pharmaceutical compositions of the present invention can be prepared in a conventional solid or liquid carrier or diluent and a conventional pharmaceutically-made adjuvant at suitable dosage level in a known way. The preferred preparations are adapted for oral application. These administration forms include, for example, pills, tablets, film tablets, coated tablets, capsules, powders and deposits.

Furthermore, the present invention also includes pharmaceutical preparations for parenteral application, including dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application, which preparations in addition to typical vehicles and/or diluents contain potassium 2-[(4S)-8-fluoro-2-[4-(3-methoxyphenyl)-piperazin-1-yl]-3-[2-methoxy-5-(trifluoromethyl)phenyl]-4H-quinazolin-4-yl]acetate or a solvate thereof.

The pharmaceutical compositions containing potassium 2-[(4S)-8-fluoro-2-[4-(3-methoxyphenyl)-piperazin-1-yl]-3-[2-methoxy-5-(trifluoromethyl)phenyl]-4H-quinazolin-4-yl]acetate or a solvate thereof according to the present invention as active ingredient will typically be administered together with suitable carrier materials selected with respect to the intended form of administration, i.e. for oral administration in the form of tablets, capsules (either solid filled, semi-solid filled or liquid filled), powders for constitution, extrudates, deposits, gels, elixirs, dispersable granules, syrups, suspensions, and the like, and consistent with conventional pharmaceutical practices. For example, for oral administration in the form of tablets or capsules, the active drug component may be combined with any oral non-toxic pharmaceutically acceptable carrier, preferably with an inert carrier like lactose, starch, sucrose, cellulose, magnesium stearate, dicalcium phosphate, calcium sulfate, talc, mannitol, ethyl alcohol (liquid filled capsules) and the like. Moreover, suitable binders, lubricants, disintegrating agents and coloring agents may also be incorporated into the tablet or capsule. Powders and tablets may contain about 5 to about 95 weight % of the inventive potassium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate of formula (I) or a solvate thereof as active ingredient.

Suitable binders include starch, gelatin, natural sugars, corn sweeteners, natural and synthetic gums such as acacia, sodium alginate, carboxymethylcellulose, polyethylene glycol and waxes. Among suitable lubricants there may be mentioned boric acid, sodium benzoate, sodium acetate, sodium chloride, and the like. Suitable disintegrants include starch, methylcellulose, guar gum, and the like. Sweetening and flavoring agents as well as preservatives may also be included, where appropriate. The disintegrants, diluents, lubricants, binders etc. are discussed in more detail below.

Moreover, the pharmaceutical compositions of the present invention may be formulated in sustained release form to provide the rate controlled release of any one or more of the components or active ingredients to optimize the therapeutic effect(s), e.g. antihistaminic activity and the like. Suitable dosage forms for sustained release include tablets having layers of varying disintegration rates or controlled release polymeric matrices impregnated with the active components and shaped in tablet form or capsules containing such impregnated or encapsulated porous polymeric matrices.

Liquid form preparations include solutions, suspensions, and emulsions. As an example, there may be mentioned water or water/propylene glycol solutions for parenteral injections or addition of sweeteners and opacifiers for oral solutions, suspensions, and emulsions. Liquid form preparations may also include solutions for intranasal administration. Aerosol preparations suitable for inhalation may include solutions and solids in powder form, which may be present in combination with a pharmaceutically acceptable carrier such as an inert, compressed gas, e.g. nitrogen. For preparing suppositories, a low melting fat or wax, such as a mixture of fatty acid glycerides like cocoa butter is melted first, and the active ingredient is then dispersed homogeneously therein e.g. by stirring. The molten, homogeneous mixture is then poured into conveniently sized moulds, allowed to cool, and thereby solidified.

Also included are solid form preparations, which are intended to be converted, shortly before use, to liquid form preparations for either oral or parenteral administration. Such liquid forms include solutions, suspensions, and emulsions.

Potassium 2-[(4S)-8-fluoro-2-[4-(3-methoxyphenyl)piperazin-1-yl]-3-[2-methoxy-5-(tri-fluoromethyl)phenyl]-4H-quinazolin-4-yl]acetate or a solvate thereof according to the invention may also be delivered transdermally. The transdermal compositions may have the form of a cream, a lotion, an aerosol and/or an emulsion and may be included in a transdermal patch of the matrix or reservoir type as is known in the art for this purpose.

The term capsule as recited herein refers to a specific container or enclosure made e.g. of methyl cellulose, polyvinyl alcohols, or denatured gelatins or starch for holding or containing compositions comprising the active ingredient (s). Capsules with hard shells are typically made of blended of relatively high gel strength gelatins from bones or pork skin. The capsule itself may contain small amounts of dyes, opaquing agents, plasticisers and/or preservatives. Under tablet a compressed or moulded solid dosage form is understood, which comprises the active ingredients with suitable diluents. The tablet may be prepared by compression of mixtures or granulations obtained by wet granulation, dry granulation, or by compaction well known to a person of ordinary skill in the art.

Oral gels refer to the active ingredients dispersed or solubilized in a hydrophilic semi-solid matrix. Powders for constitution refers to powder blends containing the active ingredients and suitable diluents which can be suspended e.g. in water or in juice.

Suitable diluents are substances that usually make up the major portion of the composition or dosage form. Suitable diluents include sugars such as lactose, sucrose, mannitol, and sorbitol, starches derived from wheat, corn rice, and potato, and celluloses, such as microcrystalline cellulose. The amount of diluent in the composition can range from about 5 to about 95% by weight of the total composition, preferably from about 25 to about 75 weight %, and more preferably from about 30 to about 60 weight %.

The term disintegrants refers to materials added to the composition to support break apart (disintegrate) and release the pharmaceutically active ingredients of a medicament. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium crosscarmellose, alginates such as alginic acid and sodium alginate, clays such as bentonites, and effervescent mixtures. The amount of disintegrant in the composition may range from about 2 to about 20 weight % of the composition, more preferably from about 5 to about 10 weight %.

Binders are substances which bind or "glue" together powder particles and make them cohesive by forming granules, thus serving as the "adhesive" in the formulation. Binders add cohesive strength already available in the diluent or bulking agent. Suitable binders include sugars such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate. The amount of binder in the composition may range from about 2 to about 20 weight % of the composition, preferably from about 3 to about 10 weight %, and more preferably from about 3 to about 6 weight %.

Lubricants refer to a class of substances, which are added to the dosage form to enable the tablet granules etc. after being compressed to release from the mould or die by reducing friction or wear. Suitable lubricants include metallic stearates such as magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine. Lubricants are usually added at the very last step before compression, since they must be present at the surface of the granules. The amount of lubricant in the composition may range from about 0.2 to about 5 weight % of the composition, preferably from about 0.5 to about 2 weight %, and more preferably from about 0.3 to about 1.5 weight % of the composition.

Glidents are materials that prevent caking of the components of the pharmaceutical composition and improve the flow characteristics of granulate so that flow is smooth and uniform. Suitable glidents include silicon dioxide and talc. The amount of glident in the composition may range from about 0.1 to about 5 weight % of the final composition, preferably from about 0.5 to about 2 weight %.

Coloring agents are excipients that provide coloration to the composition or the dosage form. Such excipients can include food grade dyes adsorbed onto a suitable adsorbent such as clay or aluminum oxide. The amount of the coloring agent may vary from about 0.1 to about 5 weight % of the composition, preferably from about 0.1 to about 1 weight %.

The inventive potassium salt of letermovir and solvates thereof exhibit an antiviral effect against representatives of the Herpes viridae group (herpes viruses), above all against the cytomegaloviruses (CMV), in particular against the human cytomegalovirus (HCMV). They are thus suitable for use in methods of treating and preventing diseases, especially infections with viruses, in particular the viruses referred to herein and the infectious diseases caused by them. The term "virus infection" is understood here to mean not only an infection with a virus but also a disease caused by infection with a virus.

Thus, another aspect of this invention refers to a pharmaceutical composition comprising the crystalline potassium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate or a solvate thereof for use in a method of treatment and/or prevention of infectious diseases caused and/or associated by cytomegalovirus, particularly human cytomegalovirus.

In another aspect, the invention relates to a pharmaceutical composition comprising the crystalline potassium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate or a solvate thereof for the preparation of a medicament for the treatment and/or prevention of diseases, in particular of virus infections, preferably human cytomegalovirus (HCMV) infections or infections with another member of the herpes viridae group.

Further, the invention provides a method of treating and/or preventing a disease associated with and/or caused by cytomegalovirus (CMV), particularly human cytomegalovirus (HCMV), or infections with another member of the herpes viridae group which comprises administering to said subject a therapeutically effective amount of the pharmaceutical composition comprising the crystalline potassium 2-[(4S)-8-fluoro-2-[4-(3-methoxyphenyl)-piperazin-1-yl]-3-[2-methoxy-5-(trifluoromethyl)phenyl]-4H-quinazolin-4-yl]acetate or a solvate thereof.

The term "effective amount" means an amount of compound that, when administered to a subject in need of such treatment, is sufficient to (i) treat or prevent a particular disease, condition, or disorder;

(ii) attenuate, ameliorate, or eliminate one or more symptoms of the particular disease, condition, or disorder; or (iii) prevent or delay the onset of one or more symptoms of the particular disease, condition, or disorder described herein.

The amount of potassium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate or a solvate thereof that will correspond to such an amount will vary depending upon factors such as the particular compound, disease condition and its severity, the identity (e.g., weight) of the subject in need of treatment, but can nevertheless be routinely determined by one skilled in the art.

Abbreviations h hour(s)
DSC differential scanning calorimetry
DVS dynamic vapour sorption
HPLC high pressure liquid chromatography min. minutes
NMR nuclear magnetic resonance
PDF pair distribution function
TGA thermogravimetric analysis
PXRD powder X-ray diffraction

Figure 1:
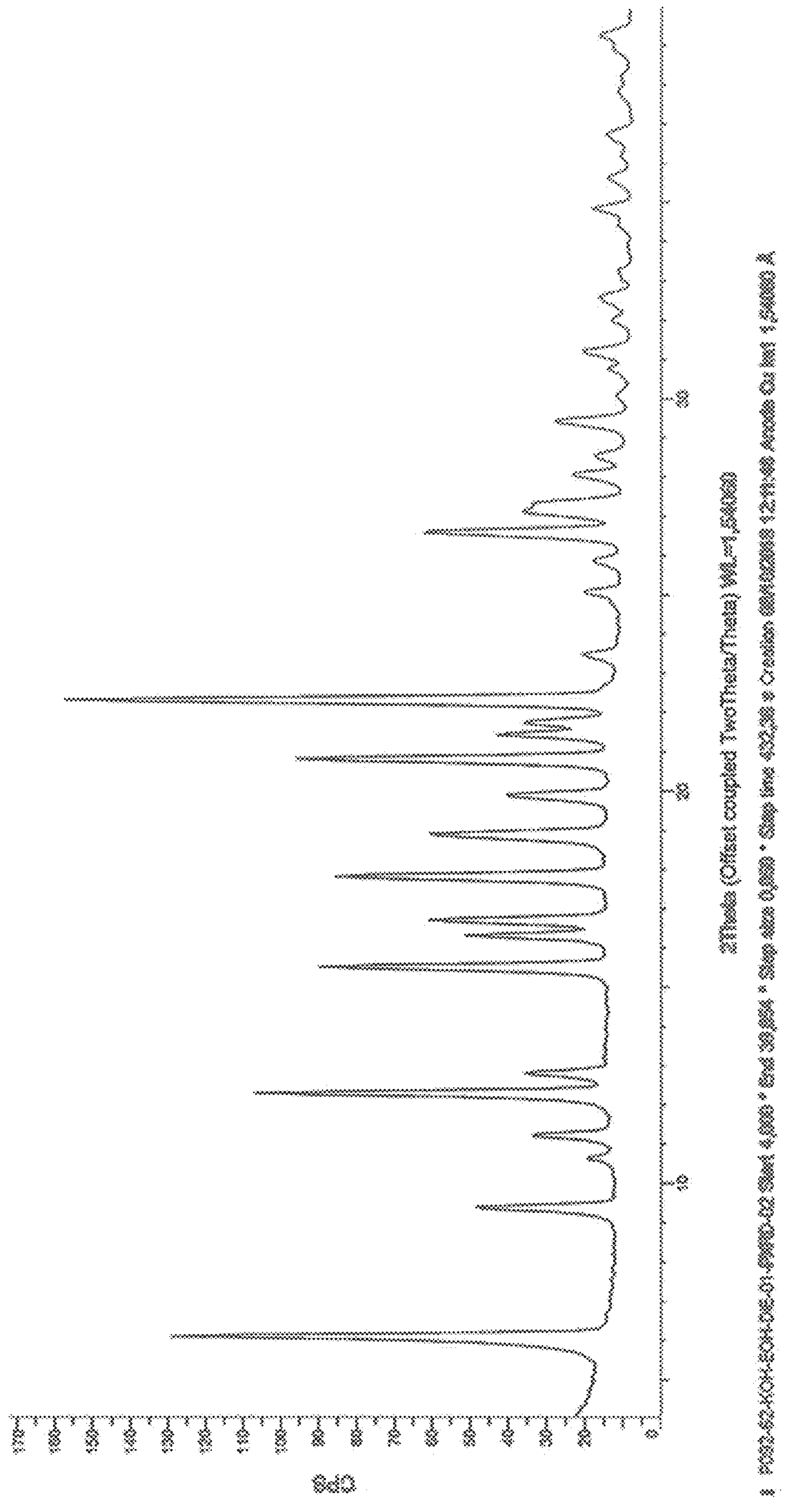
FIG. 1 shows PXRD of the obtained letermovir potassium mixed solvate.
Figure 2:
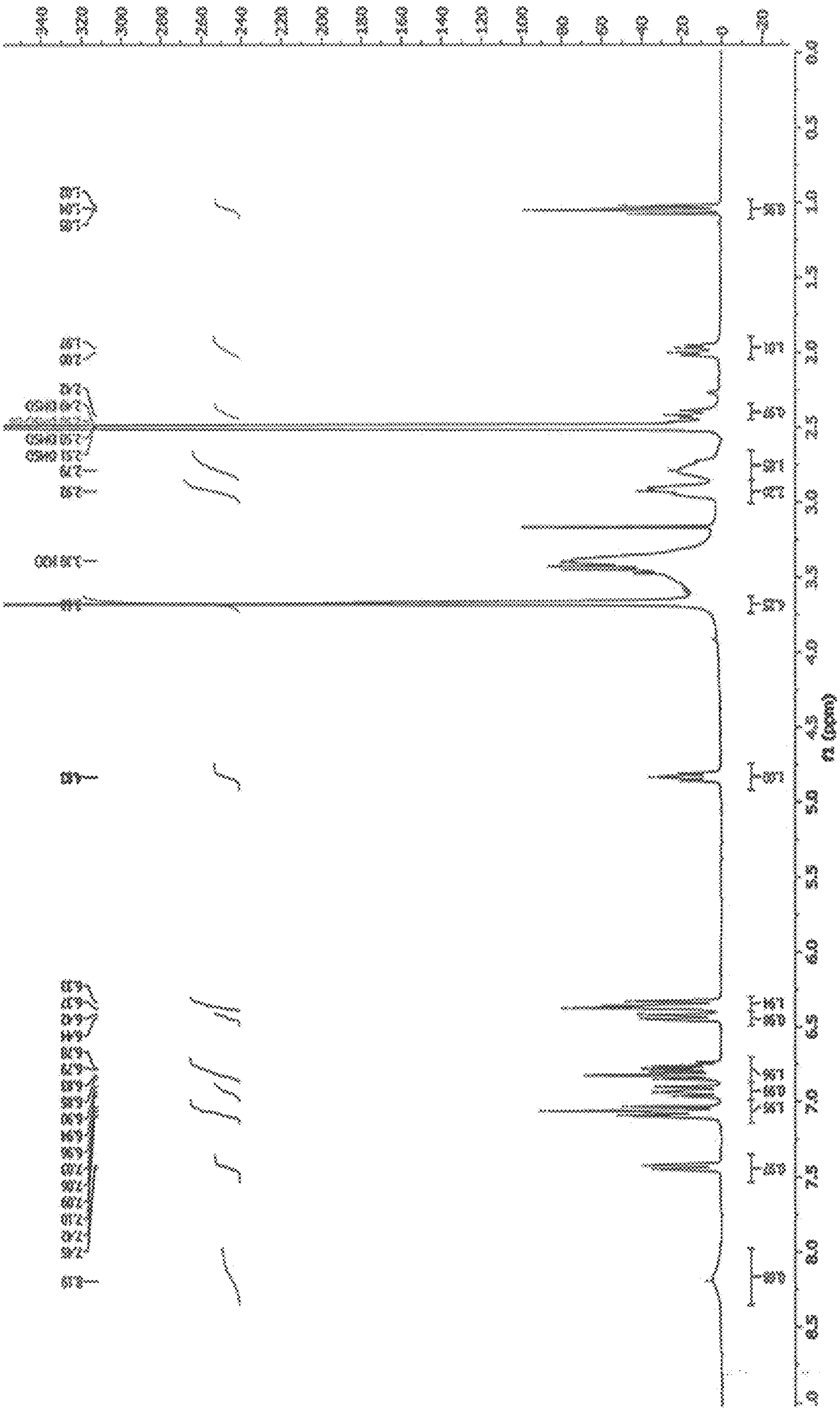
FIG. 2 shows $^{1}$H-NMR spectrum of the letermovir potassium mixed solvate.
Figure 3:
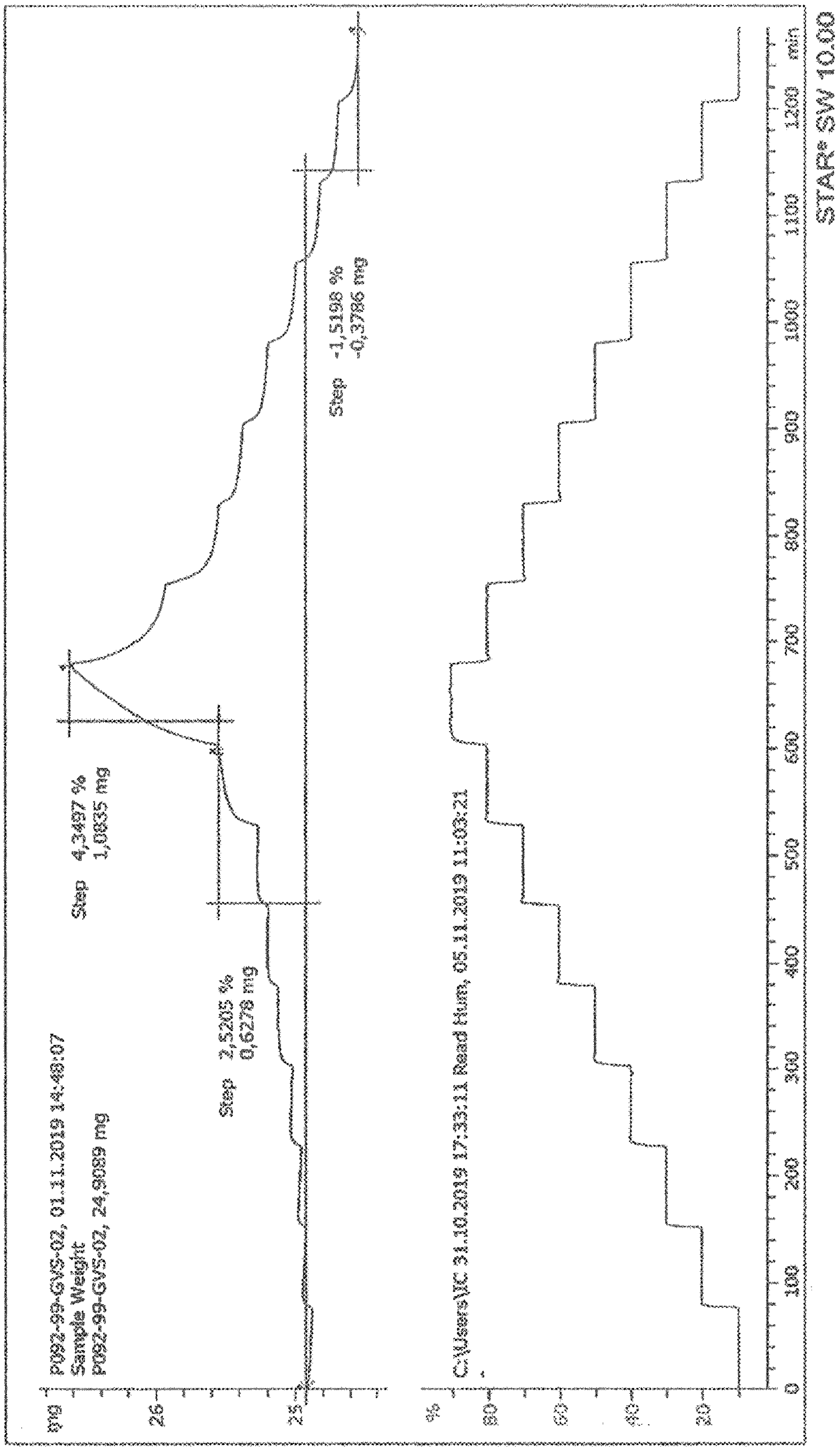
FIG. 3 shows DVS of the letermovir potassium mixed solvate. The black trace indicates the weight of the sample against time and the blue trace the relative humidity against time.
Figure 4:
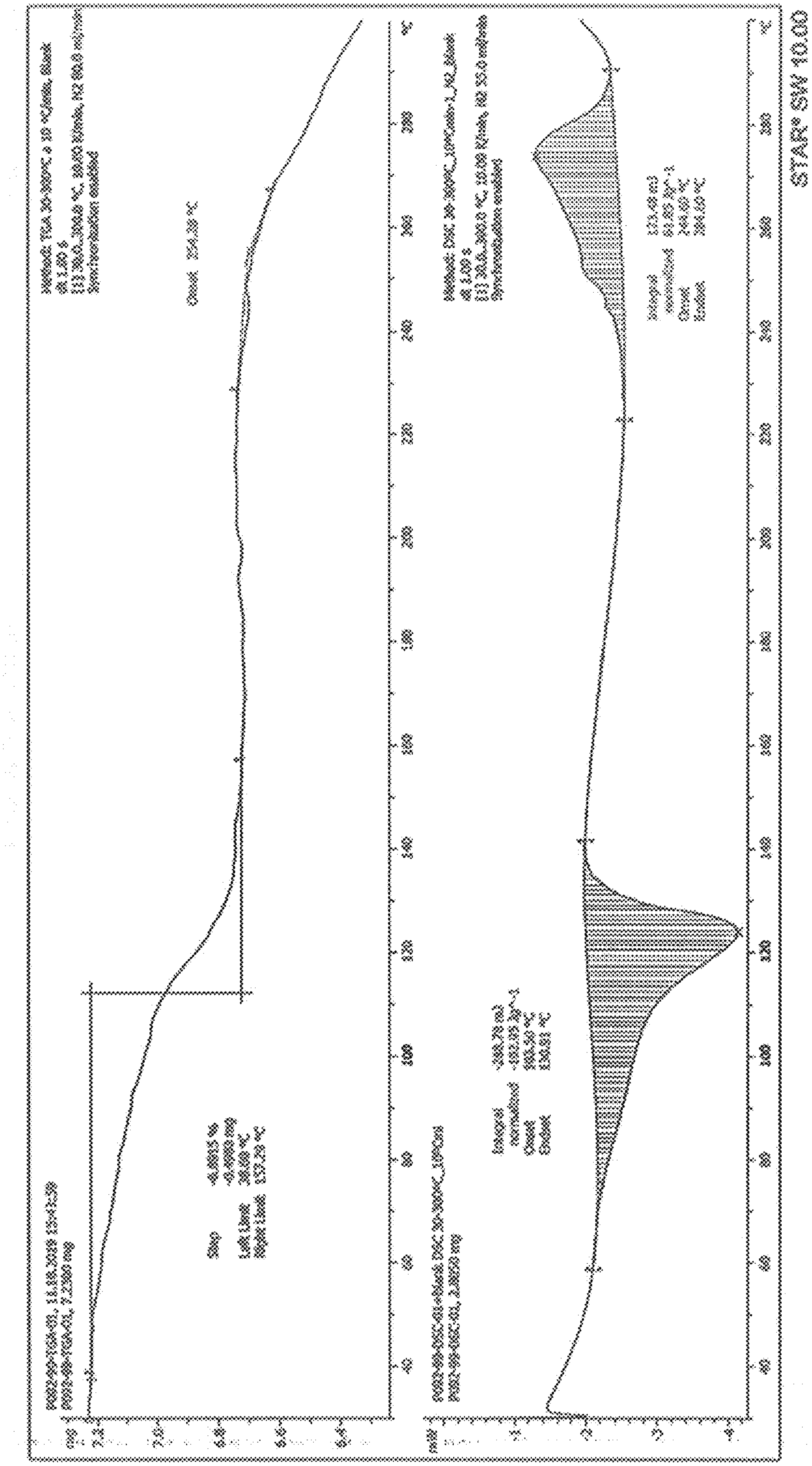
FIG. 4 shows TGA and DSC analyses of the letermovir potassium mixed solvate.
Figure 5:
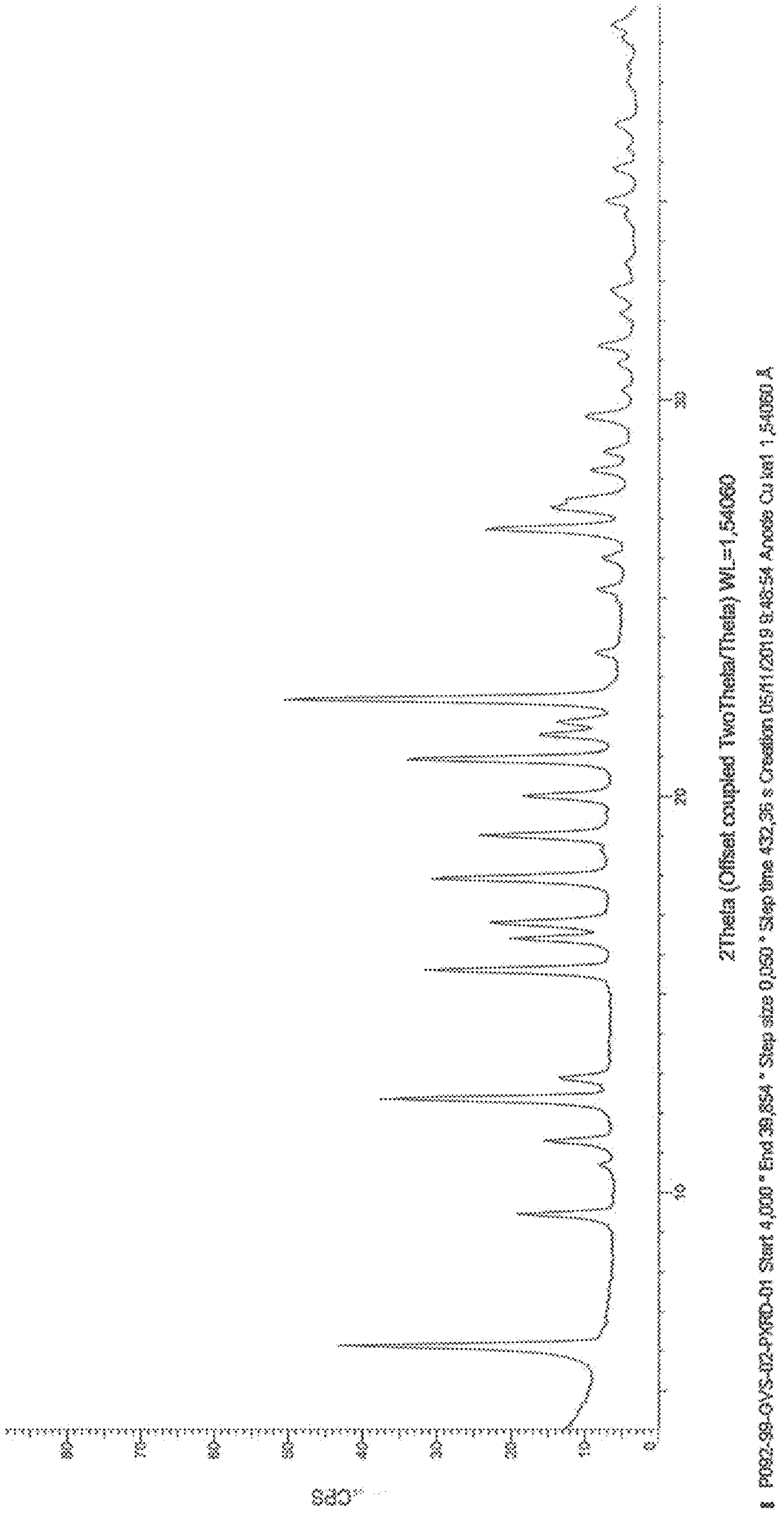
FIG. 5 shows PXRD of the obtained letermovir potassium hydrate.
Figure 6:
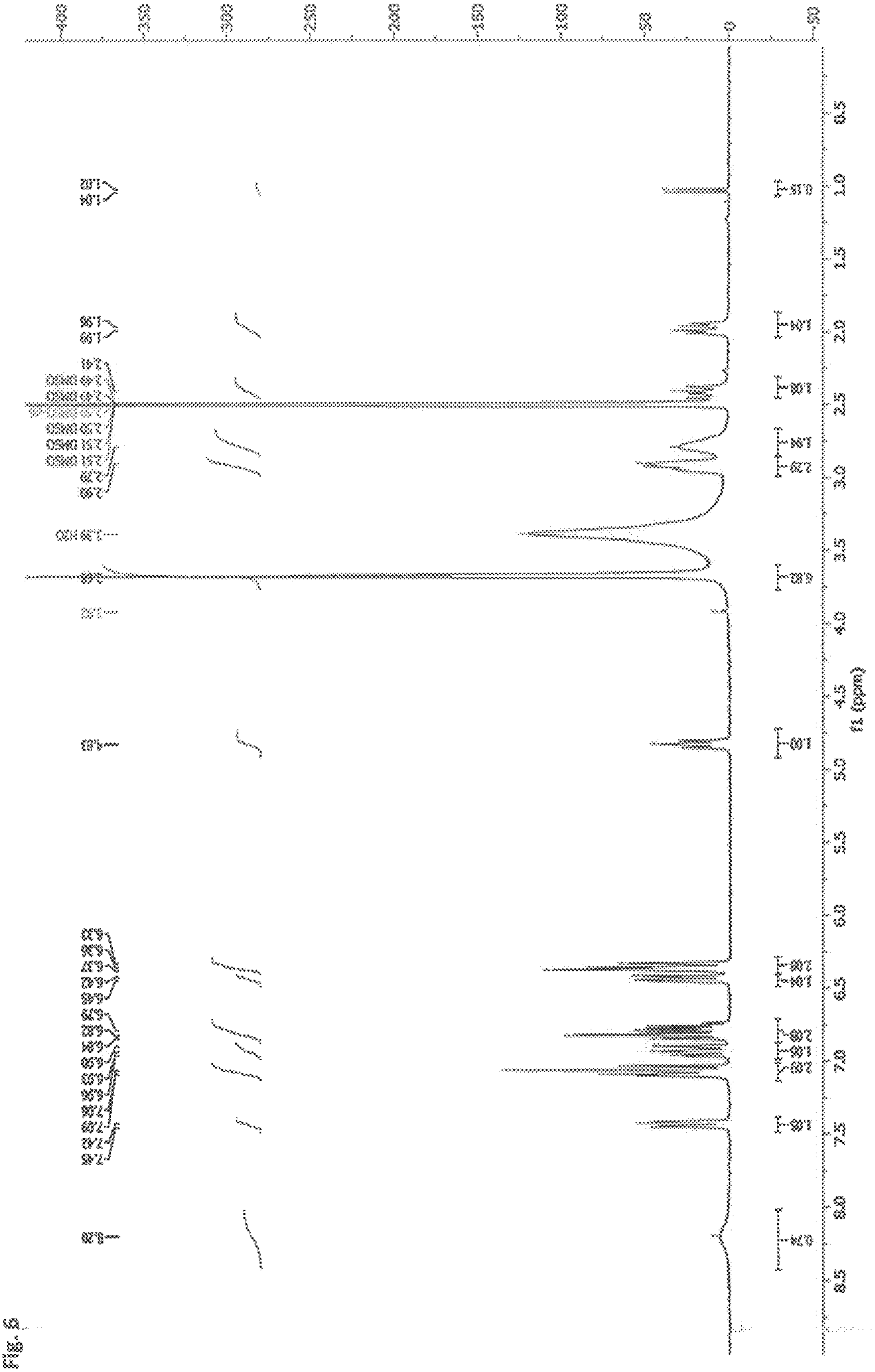
FIG. 6 shows $^{1}$H-NMR spectrum of the letermovir potassium hydrate.
Figure 7:
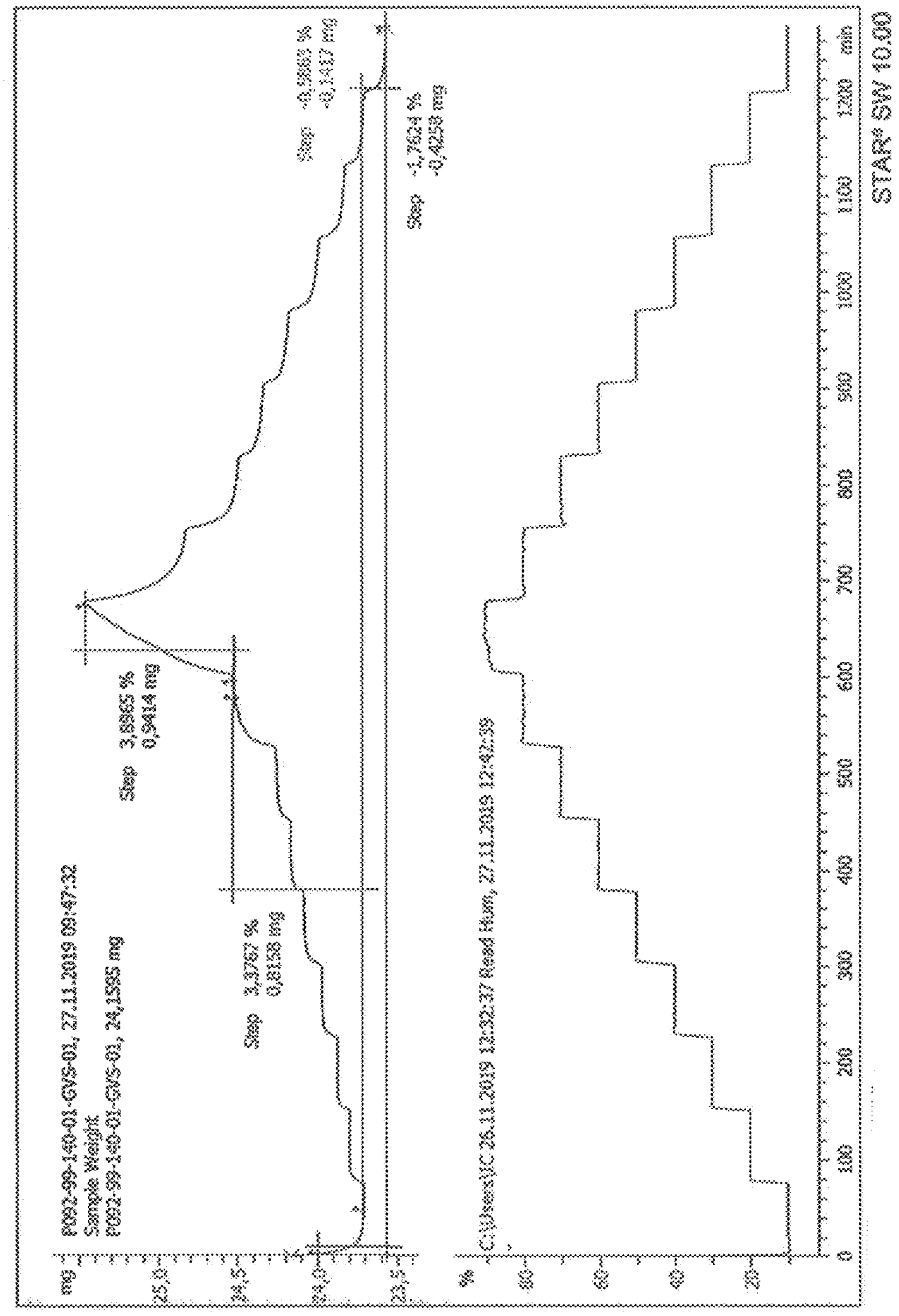
FIG. 7 DVS of the letermovir potassium hydrate. The black trace indicates the weight of the sample against time and the blue trace the relative humidity against time.
Figure 8:
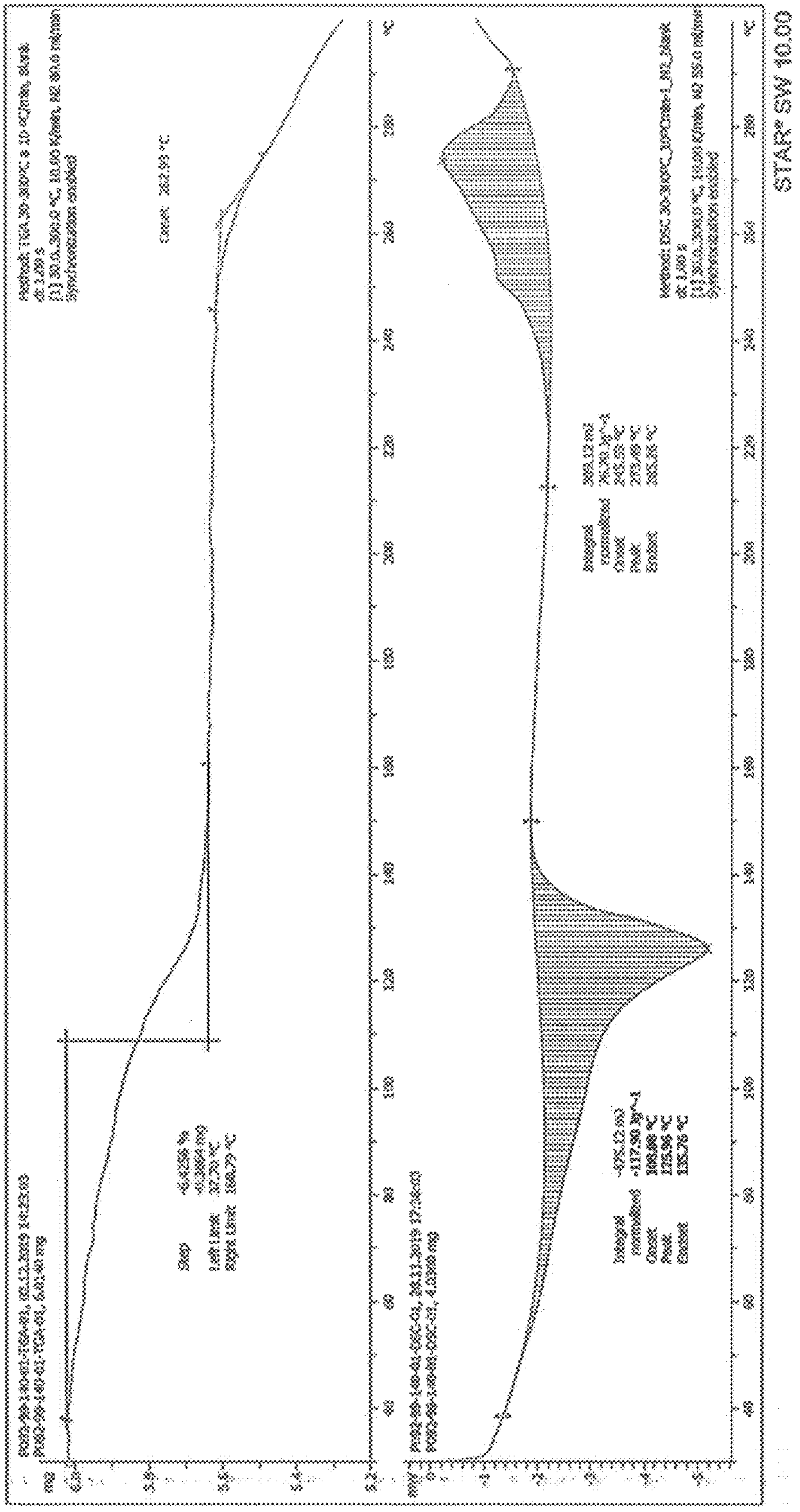
FIG. 8 TGA and DSC analyses of the letermovir potassium hydrate.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Methods and Equipment

Powder X-Ray Diffraction analysis (PXRD): Approximately 20 mg of sample were prepared in standard sample holders using two foils of polyacetate. The samples were analysed without further manipulation. Powder diffraction patterns were acquired on a D8 Advance Series 2Theta/Theta powder diffraction system using $Cu_{K\alpha 1}$-radiation (1.54060 Å) in transmission geometry. The system was equipped with a VÅNTEC-1 single photon counting PSD, a Germanium monochromator, a ninety positions autochanger sample stage, fixed divergence slits and a radial soller. The generator intensity for the generation of the X-ray beam is set to 40 mA and 40 kV. Programs used: Data collection with DIFFRAC plus XRD Commander V.2.5.1, and evaluation with EVA V.14.0.0.0 (Bruker-AXS 1996-2007) and EVA V.5.0.0.22 (Bruker-AXS 2010-2018). The samples were measured at room temperature in 0.5 hours measurement in a range from 4 to 40° in 2θ using an angular step of 0.0490 and a time per step of 2787 s.

Proton nuclear magnetic resonance spectroscopy ($^{1}$H-NMR): Proton nuclear magnetic resonance analyses were recorded in deuterated DMSO (DMSO-$d_6$) in a Bruker Avance 400 Ultrashield NMR spectrometer. Spectra were acquired solving 8-10 mg of sample in 0.6 mL of deuterated solvent.

Differential scanning calorimetry analysis (DSC): Approximately 1-4 mg of sample were weighed (using a MX5 Mettler Toledo microbalance) into 40 μL aluminium crucibles with a pinhole lid. DSC analyses were recorded in a Mettler Toledo DSC822e calorimeter. Programs used: Data collection and evaluation with software STARe. The samples were heated under dry nitrogen (flow rate: 50 mL/min) at 10° C./min from 30 to 300° C.

Thermogravimetric analysis (TGA): Approximately 1-4 mg of sample were weighed (using a MX5 Mettler Toledo microbalance) into 40 μL aluminium crucibles with a pinhole lid. Thermogravimetric analyses were recorded in a Mettler Toledo TGA/SDTA851 with a balance MT1 type. Programs used: Data collection and evaluation with software STARe. The samples were heated under dry nitrogen (flow rate: 10 mL/min) at 10° C./min from 30 to 300° C.

Dynamic Vapour Sorption (DVS): Approximately 10-20 mg of sample were weighed into 150 μL platinum crucibles without lid. The experiments were performed in a Mettler Toledo TGA/DSC 1 LF instrument equipped with a LF SDTA FRS2 sensor and coupled with a Modular Humidity Generator MHG 32. Data collection and evaluation was done with STARe software.

Single Crystal X-ray Diffraction (SCXRD): The measured crystal was selected using a Zeiss stereomicroscope using polarized light and prepared under inert conditions immersed in perfluoropolyether as protecting oil for manipulation. Crystal structure determination was carried out using a Rigaku diffractometer equipped with a Pilatus 200K area detector, a Rigaku MicroMax-007HF microfocus rotating anode with $MoK_{\alpha}$ radiation, Confocal Max Flux optics and an Oxford Cryosystems low temperature device Cryostream 700 plus (T=−173° C.). Full-sphere data collection was used with ω and φ scans. Programs used: Data collection and reduction with CrysAlisPro (Rigaku OD, 2015). V/0.60 A and absorption correction with Scale3 Abspack scaling algorithm (CrysAlisPro 1.171.39.12b (Rigaku OD, 2015)). Crystal structure solution was achieved using the computer program SHELXT (Sheldrick, G. M. *Acta Cryst.* 2015 A71, 3-8.) and visualized using the program SHELXle (C. B. Huebschle, G. M. Sheldrick & B. Dittrich; *J. Appl. Cryst.,* 2011 44, 1281-1284). Missing atoms were subsequently located from difference Fourier synthesis and added to the atom list. Least-squares refinement on $F_0^2$ using all measured intensities was carried out using the program SHELXL 2015 (SHELXL; Sheldrick, G. M. *Acta Cryst.,* 2015 A71, 3-8.). All non-hydrogen atoms were refined including anisotropic displacement parameters. High Performance Liquid Chromatography (HPLC):

Instrument: Thermo Scientific Ultimate 3000 UHPLC
Column: Agilent Zorbax Eclipse XDB C-18, 150×4.6 mm, 5 μm
Flow rate: 1.0 ml/min
Solvent A: 0.1% formic acid in water
Solvent B: 0.1% formic acid in 100% methanol
Stop time: 27 minutes
Injection volume: 10 μl
Column temperature: 35° C.
Wavelength: 260 nm
Autosampler temperature: 10° C.

TABLE 1

Gradient applied during RP-HPLC analysis.

| Time [min] | Eluent B [%] |
|---|---|
| 0.00 | 5.0 |
| 1.00 | 5.0 |
| 20.00 | 95.0 |
| 23.00 | 95.0 |
| 23.10 | 5.0 |
| 26.00 | 5.0 |

Example 1: Preparation of Letermovir Potassium Mixed Solvate

Letermovir free base (10 g, 17 mmol) was dissolved in a mixture of ethanol and diisopropyl ether (1:1, 39 mL). Afterwards, potassium hydroxide was added (0.922 g, 16 mmol) and the obtained mixture was heated to 50° C. and stirred for 3 hours. The mixture was cooled to room temperature and stirred overnight. The solvent was evaporated (rotary evaporator) and the resulting foam was stirred at room temperature for 2 hours with additional diisopropyl ether (25 mL). The resulting paste crystallizes overnight as a mixed water-ethanol solvate. The obtained solid was characterized by PXRD, $^1$H-NMR, DVS, TGA and DSC (FIGS. 1-4).

Example 2: Preparation of the Letermovir Potassium Hydrate

Potassium salt of letermovir water-ethanol mixed solvate (2.75 g, obtained in Example 1) was stored in a climatic chamber at 25° C. and 70% of relative humidity for 3 days. The hydrated form without ethanol was obtained. The obtained solid was characterized by PXRD, $^1$H-NMR, DVS, TGA and DSC (FIGS. 5-8).

Example 3: Preparation of Single Crystal of Letermovir Potassium Hydrate

Potassium salt of letermovir water-ethanol mixed solvate which was obtained in Example 1 was dissolved in methanol (MOH), ethanol (EOH), isopropyl acetate (AIP), ethyl acetate (AET), tetrahydrofuran (THF), toluene (TOL), 2-butanone (MEC) and methyl acetate (MAC). Antisolvent diisopropyl ether (DIE) was added and the sample were kept at room temperature for 48 h.

Suitable single crystals were obtained in the experiment with isopropyl acetate (AIP) and its structure was determined at 100 K by single crystal X-ray diffraction analysis.

Figure 9:
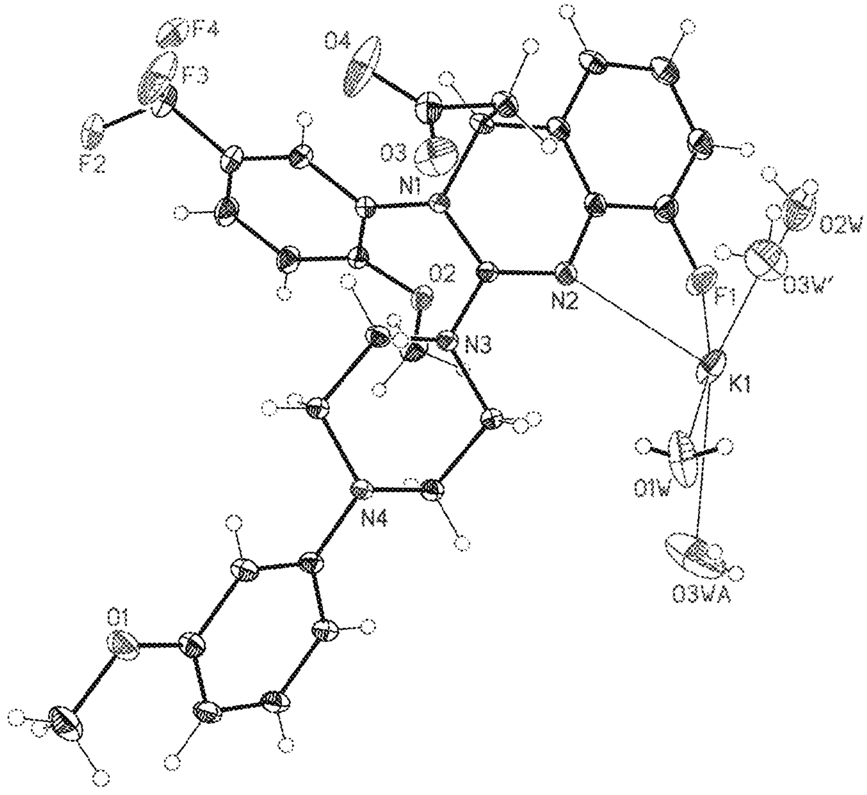
FIG. 9 shows single crystal X-ray structure of letermovir potassium hydrate. One molecule of letermovir with one potassium atom and two and a half water molecules. Some water molecules represented in the figure are shared with the contiguous cell.
Figure 10:
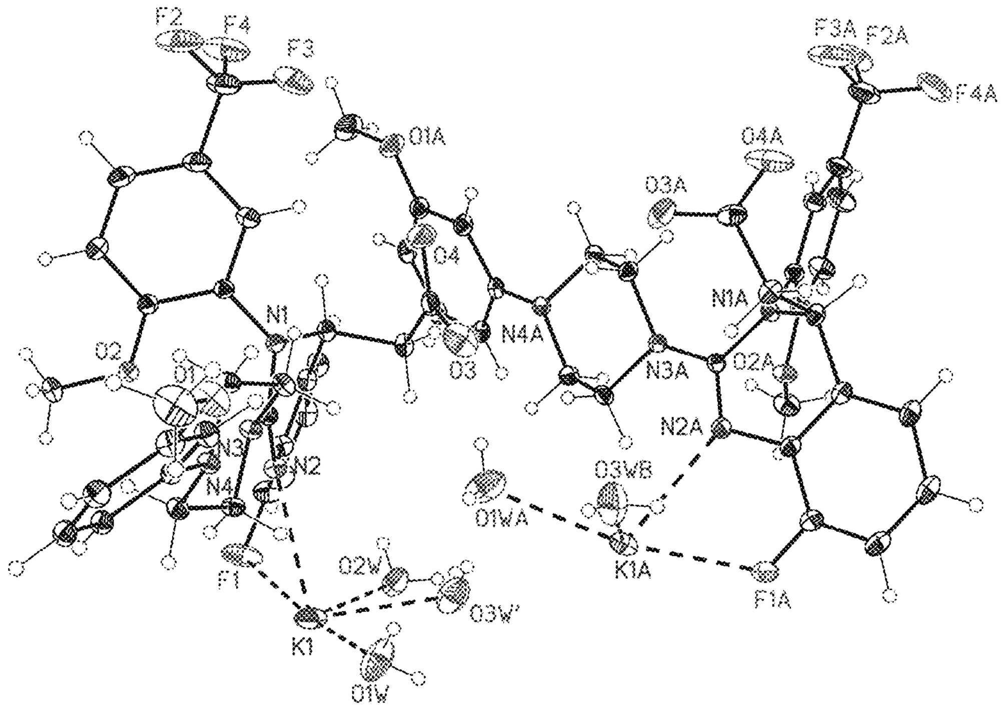
FIG. 10 shows single crystal X-ray structure of letermovir potassium hydrate. Two molecules of letermovir are present with two potassium atoms and five water molecules.
Figure 11:
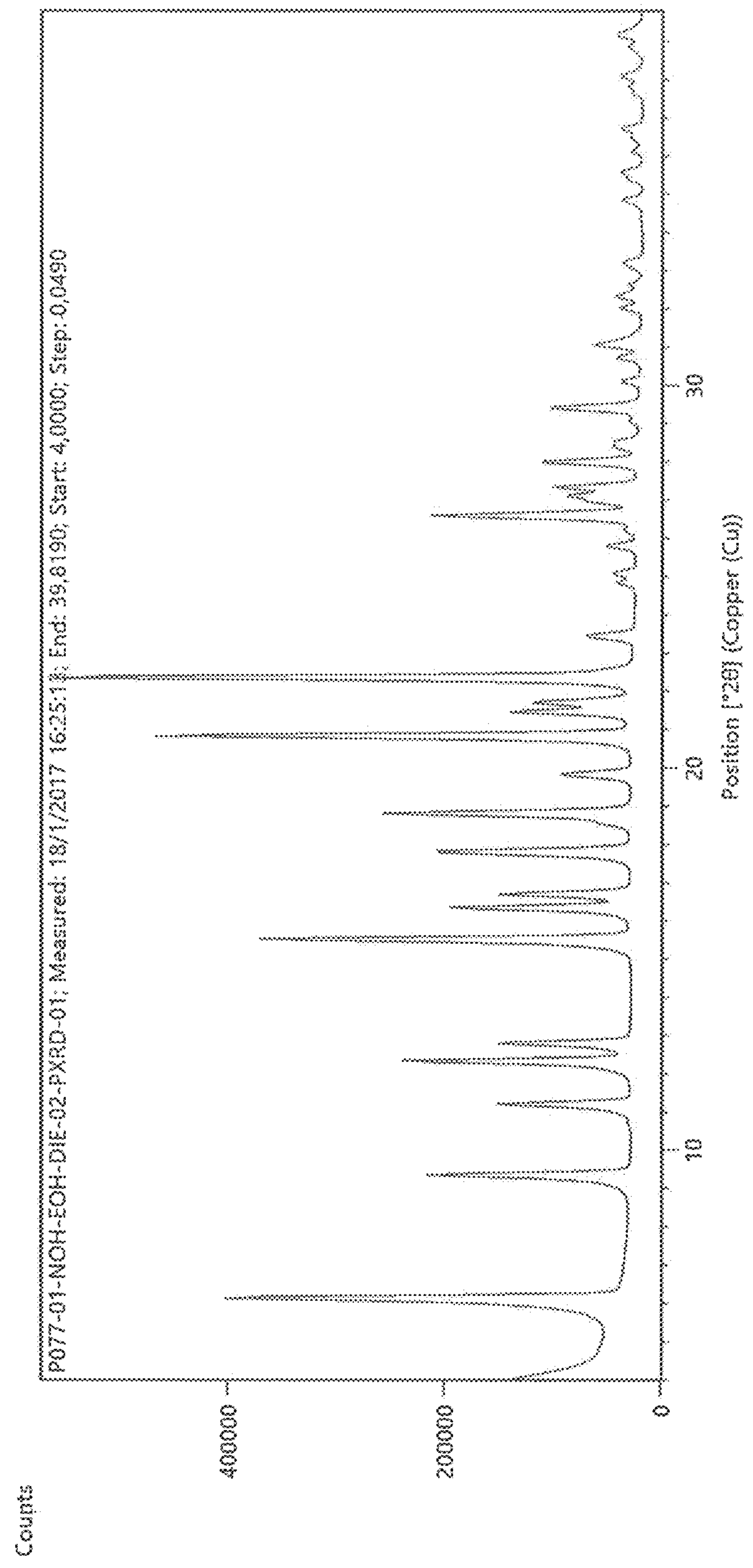
FIG. 11 shows PXRD of the obtained letermovir sodium mixed solvate.
Figure 12:
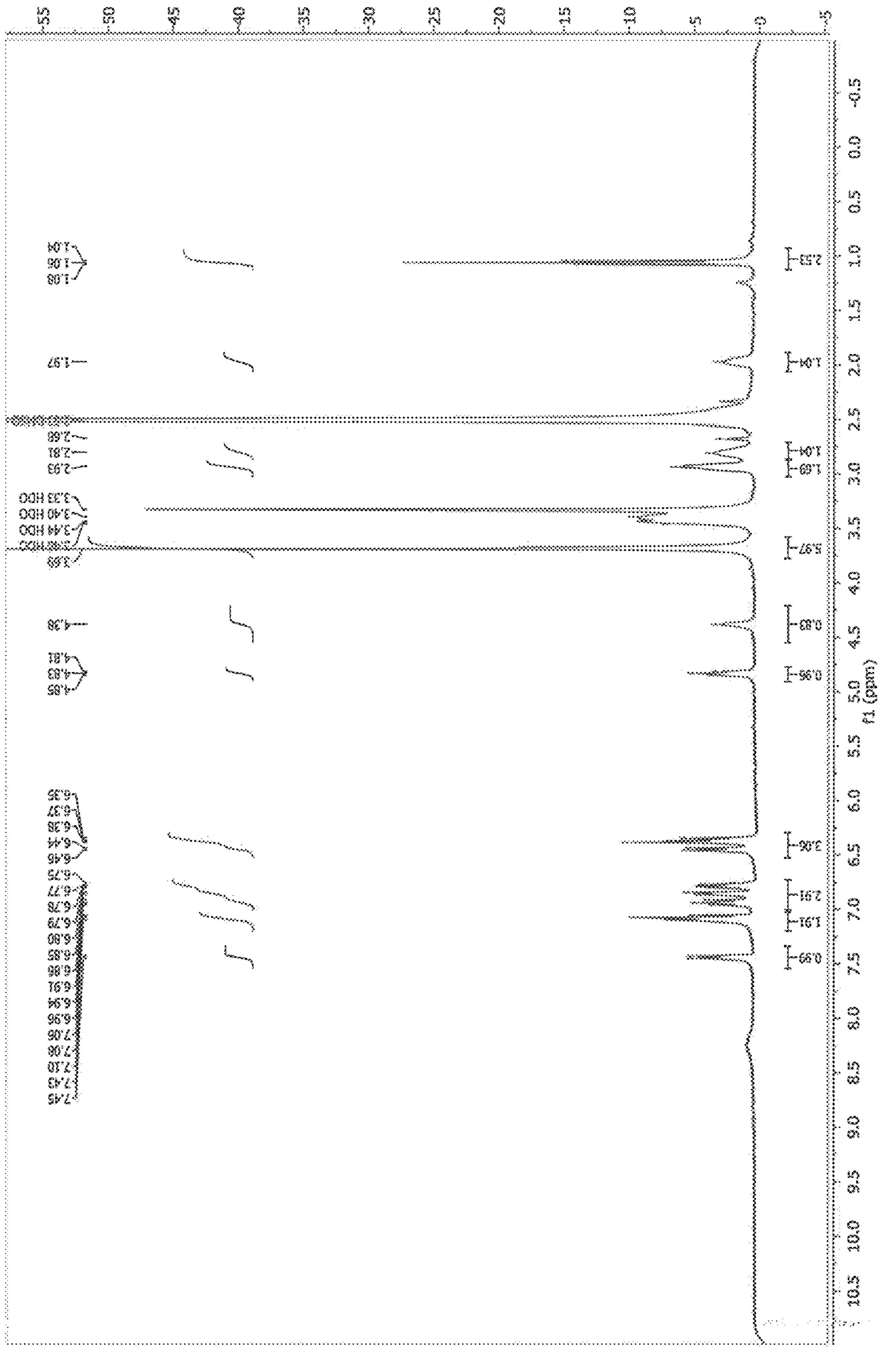
FIG. 12 shows $^{1}$H-NMR spectrum of the letermovir sodium mixed solvate.
Figure 13:
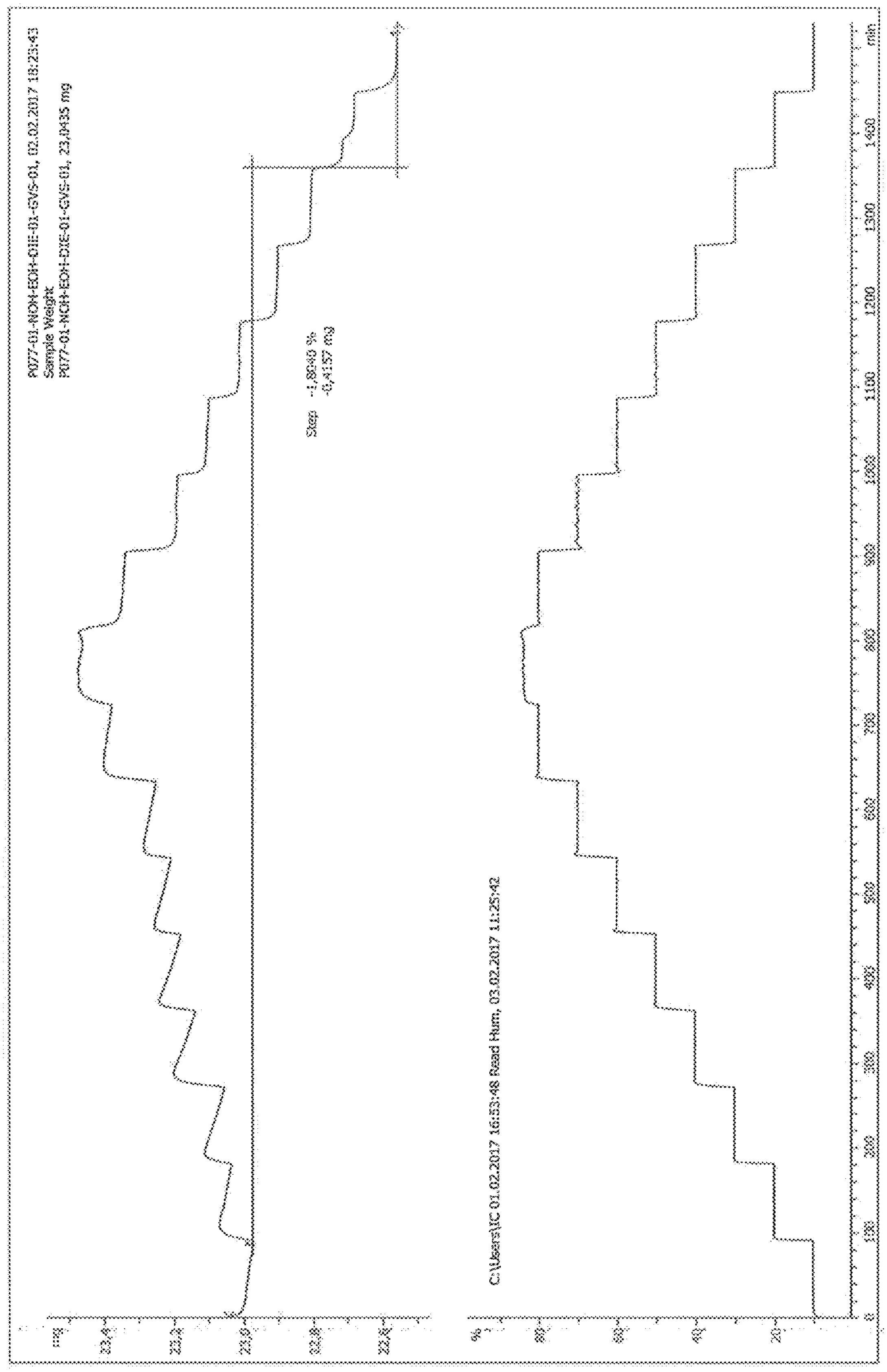
FIG. 13 shows DVS of the letermovir sodium mixed solvate. The black trace indicates the weight of the sample against time and the blue trace the relative humidity against time.
Figure 14:
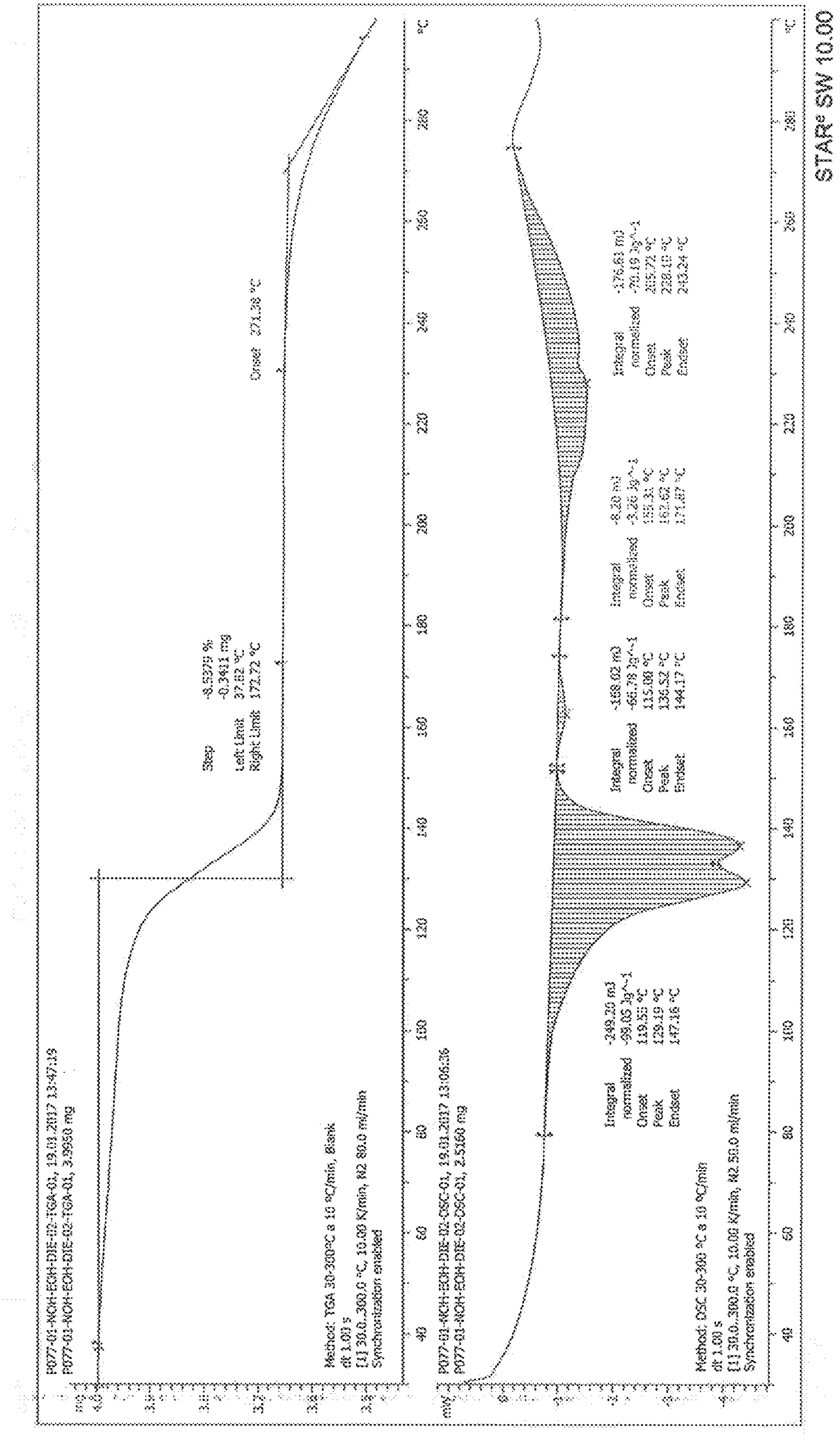
FIG. 14 shows TGA and DSC analyses of the letermovir sodium mixed solvate.

Single crystal X-ray structure is represented in FIGS. 9 and 10. A summary of the unit cell constants is given in Table 2. The single crystal structure indicates that the obtained potassium salt is a hydrate with 2.5 water molecules. The asymmetric unit contains one molecule of the organic compound and 2.5 water molecules (FIG. 9) that can be seen also as two molecules of the organic compound and 5 water molecules (FIG. 10).

TABLE 2

Cell parameters of letermovir potassium hydrate at 100 K.

| | | |
|---|---|---|
| Crystal system: | Trigonal | |
| Space group: | R3 | |
| Unit cell dimensions: | a = 28.2667(3) Å | α = 90° |
| | b = 28.2667(3) Å | β = 90° |
| | c = 10.02900(10) Å | γ = 120° |
| Volume: | 6939.66(16) Å$^3$ | |
| Density (calculated): | 1.412 mg/m$^3$ | |
| Final R indices [I > 2sigma(I)] | R1 = 0.0276, wR2 = 0.0755 | |

Reference Example 4: Preparation of Letermovir Sodium Mixed Solvate 50 g of letermovir free base were dissolved in a 1:1 mixture of ethanol and diisopropyl ether (195 mL). Ca. 3 g of NaOH were added and the mixture was heated to 50° C. and stirred for 3 h. The mixture was cooled to room temperature and stirred overnight. The volume of the resulting suspension was reduced to a half (evaporation in the rotary evaporator) and the resulting solution was stirred at room temperature for 2 hours. Additional portion of diisopropyl ether (37.5 mL) was added, and the resulting suspension was stirred at room temperature for 2 hours. The crystallized solid was filtered off and dried under vacuum at 60° C. for 2 hours, yielding 39 g (72%) of a mixed letermovir sodium water-ethanol solvate. The obtained solid was characterized by PXRD, $^1$H-NMR, DVS, TGA and DSC (FIGS. 11-14).

Example 5. Comparison of Solubilities of Letermovir Potassium Mixed Solvate and Letermovir Sodium Mixed Solvate An excess of letermovir potassium mixed solvate (the salt of Example 1) or letermovir sodium mixed solvate (the salt of Example 4) was added to 2 mL of the corresponding buffer of different pHs. The saturated suspensions were stirred for two hours at room temperature. In the case that the solid did not dissolve completely and formed a suspension, an aliquot was then filtered through a nylon syringe filter, and the obtained solution was analysed by HPLC to determine the amount of letermovir dissolved. The final pH of the mixtures was also determined.

The obtained results of the solubility tests are shown in Table 3 and 4.

TABLE 3

Solubility of the potassium salt mixed solvate and the pH of the final mixture.

| | Solubility (mg/mL) | | | Final pH | | |
|---|---|---|---|---|---|---|
| pH | Entry 1 | Entry 2 | Entry 3 | Entry 1 | Entry 2 | Entry 3 |
| 1 | 1.10 | 2.27 | | 4.5 | 6.6 | |
| 2 | 14.37 | 10.63 | | 7.2 | 7.3 | |
| 5 | 14.33 | 16.50 | | 7.1 | 7.2 | |
| 6 | 1.27 | 1.17 | | 6.3 | 6.3 | |
| 7 | 13.73 | 11.35 | >100 | 7.1 | 7.0 | 7.4 |
| 8 | >100 | >100 | | 7.7 | 7.6 | |
| 9 | >100 | >100 | | 7.7 | 7.7 | |

TABLE 4

| Solubility of the sodium salt mixed solvate and the pH of the final mixture. | | | | | |
|---|---|---|---|---|---|
| | Solubility (mg/mL) | | | Final pH | |
| pH | Entry 1 | Entry 2 | Entry 3 | Entry 1 | Entry 2 |
| 1 | 8.75 | 7.20 | | 1.4 | 1.2 |
| 2 | 0.18 | 7.04 | | 4 | 7.5 |
| 5 | 3.86 | 21.30 | | 6.8 | 7.6 |
| 6 | 0.06 | 0.02 | | 6.3 | 6.5 |
| 7 | 2.23 | >100 | >100 | 7.3 | 8 |
| 8 | >100 | | | 8.6 | — |
| 9 | >100 | | | 9.3 | — |

As can be seen from Table 3, concentration levels of above 100 mg/mL with respect to letermovir free base can be achieved by dissolving said crystalline potassium salt of letermovir in aqueous medium while maintaining the pH values in the physiological range 7.4-7.8. The pH of the final solution is stabilized by the potassium ions in the range 7.4-7.8 when the concentrations of letermovir reach 100 mg/mL. The effect is maintained even if the pH of the initial buffer is 8 or higher. These results demonstrate a clear evidence of a surprising buffering effect of the potassium ions present in equimolar ratio to letermovir free base, which allows preparing aqueous solutions with high concentrations of the active substance while keeping the pH values stable in the physiological range. Comparative experiments with the sodium salt demonstrated that with the concentration levels of letermovir of above 100 mg/mL, the pH of the solution increases from 7 to 8 and continues growing if the pH of the initial buffer is higher than 7 (Table 4).

The invention claimed is:

1. A crystalline potassium salt of letermovir (potassium 2-[(4S)-8-fluoro-2-[4-(3-methoxyphenyl)piperazin-1-yl]-3-[2-methoxy-5-(trifluoromethyl)phenyl]-4H-quinazolin-4-yl]acetate) of formula (I)

(I)

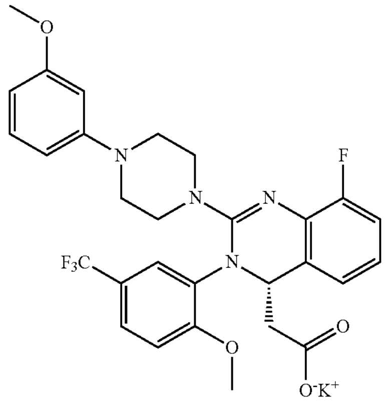

or a solvate thereof.

2. The crystalline potassium salt of letermovir or the solvate thereof according to claim 1, wherein the solvate is a hydrate.

3. The crystalline potassium salt of letermovir or the solvate thereof according to claim 1, wherein the solvate is a 2.5-hydrate.

4. The crystalline potassium salt of letermovir or the solvate thereof according to claim 1, wherein the solvate is a mixed water-ethanol solvate.

5. The crystalline potassium salt of letermovir or the solvate thereof according to claim 3, wherein said 2.5-hydrate shows characteristic peaks at about 6.1, 9.5, 10.7, 11.3, 12.4, 12.9, 15.6, 16.4, 16.8, 17.9, 19.0, 20.0, 20.9, 21.7, 22.4, 23.6, 25.2, 26.0, 26.7, 27.3, 28.2, 28.7, 29.6, 30.2, 30.9, 31.4, 32.2, 32.8 and 33.4 degrees 2theta in an X-ray powder diffractogram.

6. The crystalline potassium salt of letermovir or the solvate thereof according to claim 4, wherein said mixed water-ethanol solvate shows characteristic peaks at about 6.1, 9.4, 10.6, 11.2, 12.3, 12.8, 15.5, 16.3, 16.7, 17.8, 18.9, 19.9, 20.8, 21.7, 22.3, 23.5, 25.1, 25.9, 26.6, 27.1, 28.1, 28.5, 29.4, 30.1, 30.8, 31.2, 32.0, 32.6 and 33.3, degrees 2theta in an X-ray powder diffractogram.

7. A method of producing the crystalline potassium salt of letermovir or the solvate thereof as defined in claim 1, wherein the method comprises:

a) Dissolving 2-[(4S)-8-fluoro-2-[4-(3-methoxyphenyl)piperazin-1-yl]-3-[2-methoxy-5-(trifluoromethyl)phenyl]-4H-quinazolin-4-yl]acetic acid or a salt or a solvate thereof in a first solvent, wherein said first solvent comprises at least one C1-C6-dialkyl ether and at least one C1-C6 alcohol, optionally under heating;

b) Adding potassium hydroxide to the solution obtained in a) to provide a first mixture;

c) Stirring said first mixture obtained in b) at a temperature in the range of from 25° C. to 80° C. for at least 5 minutes;

d) Cooling said first mixture to a temperature in the range of from 0° C. to 30° C. and stirring said first mixture at said temperature for at least 10 minutes;

e) Removing said first solvent to provide a first solid;

f) Contacting said first solid with a second solvent comprising at least one C1-C6-dialkyl ether to provide a second mixture;

g) Stirring said second mixture at a temperature in the range of from 0° C. to 30° C. for at least 1 hour; and h) Removing said second solvent to provide a second solid.

8. The method according to claim 7, further comprising keeping the second solid at a temperature in the range of from 20° C. to 30° C. and at a relative humidity of at least 60% for at least 1 hour.

9. The method according to claim 7, wherein said C1-C6-dialkyl ether is diisopropyl ether.

10. The method according claim 7, wherein said C1-C6-alcohol is ethanol.

11. The method according to claim 7, wherein the ratio of volumes of C1-C6-dialkyl ether and C1-C6 alcohol in a) is in the range of from 3:1 to 1:3.

12. The method according to claim 7, wherein said first mixture is stirred in c) at a temperature in the range of from 45° C. to 55° C. for at least 30 minutes.

13. The method according to claim 7, wherein said first mixture is cooled in d) to a temperature in the range of from 20° C. to 30° C. and stirred at said temperature for at least 30 minutes.

14. The method according to claim 7, wherein said first solvent is removed in e) by evaporation.

15. The method according to claim 7, wherein said second solvent is removed in h) by filtration.

16. A crystalline potassium salt of letermovir or a solvate thereof which is obtainable by the method as defined in claim 7.

17. A pharmaceutical composition comprising the crystalline potassium salt of letermovir or the solvate thereof as defined in claim 1 and at least one pharmaceutically acceptable excipient and/or diluent.

18. A method for treatment of a virus infection comprising administering to an infected subject a pharmaceutical composition as defined in claim 17.

19. A method for treatment of a virus infection comprising administering to an infected subject the crystalline potassium salt of letermovir or the solvate thereof as defined in claim 1.

20. A method for prevention of a virus infection comprising administering to a subject a pharmaceutical composition as defined in claim 17.

21. A method for treatment of a virus infection by a member of the herpes viridae group comprising administering to an infected subject a pharmaceutical composition as defined in claim 17.

22. A method for treatment of a human cytomegalovirus (HCMV) infection comprising administering to an infected subject a pharmaceutical composition as defined in claim 17.

23. A method for treatment of a virus infection by a member of the herpes viridae group comprising administering to an infected subject the crystalline potassium salt of letermovir or the solvate thereof as defined in claim 1.

24. A method for treatment of a human cytomegalovirus (HCMV) infection comprising administering to an infected subject the crystalline potassium salt of letermovir or the solvate thereof as defined in claim 1 to the subject.

25. A method for prevention of a virus infection by a member of the herpes viridae group comprising administering to a subject a pharmaceutical composition as defined in claim 17.

26. A method for prevention of a human cytomegalovirus (HCMV) infection comprising administering to a subject a pharmaceutical composition as defined in claim 17.

27. A method for prevention of a virus infection comprising administering to a subject the crystalline potassium salt of letermovir or the solvate thereof as defined in claim 1.

28. A method for prevention of a virus infection by a member of the herpes viridae group comprising administering to a subject the crystalline potassium salt of letermovir or the solvate thereof as defined in claim 1.

29. A method for prevention of a human cytomegalovirus (HCMV) infection comprising administering to a subject the crystalline potassium salt of letermovir or the solvate thereof as defined in claim 1.

* * * * *